US008911724B2

(12) United States Patent
Kaiser

(10) Patent No.: US 8,911,724 B2
(45) Date of Patent: *Dec. 16, 2014

(54) NUTRIENT COMPOSITIONS AND METHODS FOR ENHANCED EFFECTIVENESS OF THE IMMUNE SYSTEM

(71) Applicant: K-PAX Pharmaceuticals, Inc., Mill Valley, CA (US)

(72) Inventor: Jon D. Kaiser, Mill Valley, CA (US)

(73) Assignee: K-PAX Pharmaceuticals, Inc., Mill Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/720,080

(22) Filed: Dec. 19, 2012

(65) Prior Publication Data

US 2013/0183277 A1 Jul. 18, 2013

Related U.S. Application Data

(63) Continuation of application No. 13/117,811, filed on May 27, 2011, now Pat. No. 8,361,512, which is a continuation of application No. 12/044,907, filed on Mar. 7, 2008, now Pat. No. 7,951,847, which is a continuation of application No. 10/750,545, filed on Dec. 31, 2003, now abandoned.

(51) Int. Cl.
| | |
|---|---|
| A61K 33/00 | (2006.01) |
| A61K 31/455 | (2006.01) |
| A61K 33/22 | (2006.01) |
| A61K 31/51 | (2006.01) |
| A61K 31/519 | (2006.01) |
| A23L 1/302 | (2006.01) |
| A61K 31/525 | (2006.01) |
| A23L 1/305 | (2006.01) |
| A61K 33/24 | (2006.01) |
| A61K 31/122 | (2006.01) |
| A61K 33/30 | (2006.01) |
| A61K 33/34 | (2006.01) |
| A61K 31/195 | (2006.01) |
| A61K 31/4188 | (2006.01) |
| A61K 33/26 | (2006.01) |
| A61K 33/18 | (2006.01) |
| A61K 45/06 | (2006.01) |
| A61K 31/352 | (2006.01) |
| A61K 33/04 | (2006.01) |
| A61K 31/7076 | (2006.01) |
| A61K 31/385 | (2006.01) |
| A61K 33/06 | (2006.01) |
| A61K 31/375 | (2006.01) |
| A61K 31/714 | (2006.01) |
| A61K 31/381 | (2006.01) |
| A61K 31/198 | (2006.01) |
| A23L 1/30 | (2006.01) |
| A61K 31/205 | (2006.01) |
| A23L 1/304 | (2006.01) |
| A61K 31/593 | (2006.01) |
| A61K 33/32 | (2006.01) |
| A61K 31/7056 | (2006.01) |

(52) U.S. Cl.
CPC ............... *A61K 33/34* (2013.01); *A61K 31/455* (2013.01); *A61K 33/22* (2013.01); *A61K 33/00* (2013.01); *A61K 31/51* (2013.01); *A61K 31/519* (2013.01); *A23L 1/302* (2013.01); *A61K 31/525* (2013.01); *A23L 1/3051* (2013.01); *A61K 33/24* (2013.01); *A61K 31/122* (2013.01); *A61K 33/30* (2013.01); *A61K 31/195* (2013.01); *A61K 31/4188* (2013.01); *A61K 33/26* (2013.01); *A61K 33/18* (2013.01); *A61K 45/06* (2013.01); *A61K 31/352* (2013.01); *A61K 33/04* (2013.01); *A61K 31/7076* (2013.01); *A61K 31/385* (2013.01); *A61K 33/06* (2013.01); *A61K 31/375* (2013.01); *A61K 31/714* (2013.01); *A61K 31/381* (2013.01); *A61K 31/198* (2013.01); *A23L 1/3004* (2013.01); *A61K 31/205* (2013.01); *A23L 1/304* (2013.01); *A61K 31/593* (2013.01); *A61K 33/32* (2013.01); *A61K 31/7056* (2013.01)
USPC .......... 424/94.1; 424/641; 424/646; 424/655; 424/657; 424/677; 424/702; 424/722

(58) Field of Classification Search
None
See application file for complete search history.

(56) References Cited

U.S. PATENT DOCUMENTS

| | | | |
|---|---|---|---|
| 5,895,652 | A | 4/1999 | Giampapa |
| 5,916,912 | A | 6/1999 | Ames et al. |
| 5,948,443 | A | 9/1999 | Riley et al. |

(Continued)

FOREIGN PATENT DOCUMENTS

| | | |
|---|---|---|
| WO | WO 94/02036 | 2/1994 |
| WO | WO 99/43329 | 9/1999 |

(Continued)

OTHER PUBLICATIONS

Supplementary European Search Report dated Aug. 13, 2008.

(Continued)

Primary Examiner — Ernst V Arnold
(74) Attorney, Agent, or Firm — Dickstein Shapiro LLP

(57) ABSTRACT

Provided are methods and compositions for increasing $CD4^+$ cell count in mammals, preferably by at least 25%, while undergoing treatment for various conditions whose treatment can have detrimental effects on immune system function. Such conditions include, but are not limited to, HIV infection, cancer, and hepatitis. The compositions include alpha lipoic acid; acetyl L-carnitine; N-acetyl-cysteine; and optionally: zinc, selenium, vitamin C, bioflavinoid complex, vitamin E, co-enzyme Q10, glutathione, beta-carotene, vitamin A, vitamin B1, vitamin B2, vitamin B6, niacinamide, calcium pantothenate, folic acid, vitamin B12, copper, manganese, chromium, and molybdenum.

29 Claims, 3 Drawing Sheets

(56) References Cited

U.S. PATENT DOCUMENTS

| | | | |
|---|---|---|---|
| 6,063,820 A | 5/2000 | Cavazza | |
| 6,103,756 A | 8/2000 | Gorsek | |
| 6,191,162 B1 | 2/2001 | Byrd et al. | |
| 6,284,767 B1 | 9/2001 | Sham et al. | |
| 6,365,622 B1 | 4/2002 | Cavazza | |
| 6,423,349 B1 | 7/2002 | Sherratt et al. | |
| 6,451,341 B1 | 9/2002 | Slaga et al. | |
| 6,479,069 B1 | 11/2002 | Hamilton | |
| 6,579,544 B1 | 6/2003 | Rosenberg et al. | |
| 2001/0031744 A1 | 10/2001 | Kosbab | |
| 2002/0155163 A1 | 10/2002 | Benjamin et al. | |
| 2002/0176900 A1 | 11/2002 | Yegorova | |
| 2003/0206895 A1 | 11/2003 | Cavazza | |

FOREIGN PATENT DOCUMENTS

| | | |
|---|---|---|
| WO | WO 99/11968 | 3/2000 |
| WO | WO 00/67596 | 11/2000 |
| WO | WO 00/76492 A1 | 12/2000 |

OTHER PUBLICATIONS

Patrick (Altern Med Rev 2000, 5(4), 290-305).
Patrick (Altern Med Rev 2000, 5(1), 39-51).
Nijveldt et al. (Am J Clin Nutr 2001, 74, 418-25).
Fawzi et al. (N Engl. J. Med 2004, 361, 23-32).
Kaiser et al. (J Acquir Immune Defic Syndr 2006, 42(5), 523-528).
Abbs et al. "Evaluation of the efficacy of thiamine and pyridoxine in the treatment of symptomatic diabetic peripheral neuropathy," *East Afr. Med. J.* 74(12):803-808 (1997).
Allard et al., "Effects of vitamin E and C supplementation on oxidative stress and viral load in HIV-infected subjects," *Aids* 12(13):1653-1659 (1998).
Aukrust et al., "Glutathione redox disturbances in human immunodeficiency virus infection: immunologic and therapeutic consequences," *Nutrition* 15(2):165-167 (1999).
Baur et al., "Alpha-lipoic acid is an effective inhibitor of human immuno-deficiency virus (HIV-1) replication," *Klin. Wochenschr.* 69(15):722-724 (1991).
Bernstein et al., "Brief communication: effect of pharmacologic doses of vitamin B6 on carpal tunnel syndrome, electroencephalographic results, and pain," *J. Am. Coll. Nutr.* 12(1):73-76 (1993).
Buhl et al., "Systemic glutathione deficiency in symptom-free HIV-seropositive individuals," *Lancet* 334(8675): 1294-8 (1989).
Buttke et al., "Oxidative stress as a mediator of apoptosis," *Immunol. Today* 15(1):7-10 (1994).
Campos et al., "Plasma carnitine insufficiency and effectiveness of L-carnitine therapy in patients with mitochondrial myopathy," *Muscle Nerve* 16(2):150-153 (1993).
Chen et al., "Delayed cytotoxicity and selective loss of mitochondrial DNA in cells treated with the anti-human immunodeficiency virus compound 2',3'-dideoxycytidinne," *J. Biol. Chem.* 264(20):11934-11937 (1989).
Chen et al., "Effect of anti-human immunodeficiency virus nucleoside analogs on mitochondrial DNA and its implication for delayed toxicity," *Mol. Pharmacol.* 39(5):625-628 (1991).
Choi et al., "Molecular mechanism of decreased glutathione content in human immunodeficiency virus type 1 Tat-transgenic mice," *J. Biol. Chem.* 275(5):3693-3698 (2000).
Dalakas et al., "Zidovudine-induced mitochondrial myopathy is associated with muscle carnitine deficiency and lipid storage," *Ann. Neurol.* 35(4):482-487 (1994).
De Quay et al., "Glutathione depletion in HIV-infected patients: role of cysteine deficiency and effect of oral N-acetylcysteine," *AIDS* 6(8):815-819 (1992).
Douglas Laboratories, Inc. "Energizer Formula—Nutritional Support for Mitochondrial Energy Production" (1999).
Famularo et al., "Acetyl-carnitine deficiency in AIDS patients with neurotoxicity on treatment with antiretroviral nucleoside analogues," *AIDS* 11(2):185-190 (1997).
Famularo et al., "Treatment with acetyl-L-carnitine has the potential to improve the clinical course of painful peripheral neuropathies in HIV-positives patients," *J. Peripher. Nerv. Syst.* 3(3):227-229 (1998).
Fuchs et al., "Studies on lipoate effects on blood redox state in human immunodeficiency virus infected patients," *Arzneimittelforschung* 43(12):1359-1362 (1993).
Herzenberg et al., "Glutathione deficiency is associated with impaired survival in HIV disease," *Proc. Natl. Acad. Sci. USA* 94(5):1967-1972 (1997).
Kaiser, M.D., Jon D., Healing HIV How to Rebuild Your System, Health First Press, Mill Valley, California (1999).
Kalebic et al., "Suppression of human immunodeficiency virus expression in chronically infected monocytic cells by glutathione, glutathione ester, and N-acetylcysteine," *Proc. Natl. Acad. Sci. USA* 88(3):986-990 (1991).
Khouri et al., Lactic acidosis secondary to nucleoside analog antiretroviral therapy, *Infec. Med.* 17(8):541-554 (2000).
Kuby, Immunology, 3rd Edition, W.H. Freeman & Co., New York (1997).
Packer et al., "Vitamin E and alpha-lipoate: role in antioxidant recycling and activation of the NF-kappa B transcription factor," *Mol. Aspects Med.* 14(3):229-239 (1993).
Parker et al., "Mitochondrial toxicity of antiviral nucleoside analogs," *J. NIH Res.* 6:57-61 (1994).
Patrick, ND, Lyn, "Nutrients and HIV: part three—N-acetylcysteine, alpha-lipoic acid, L-glutamine, and L-carnitine," *Altern. Med. Rev.* 5(4):290-305 (2000).
Paul, W.E., Fundamental Immunology, 3rd Edition, Raven Press, New York (1989).
Sato et al., "Thiol-mediated redox regulation of apoptosis. Possible roles of cellular thiols other than glutathione in T cell apoptosis," *J. Immunol.* 154(7):3194-3203 (1995).
Scarpini et al., "Effect of acetyl-L-carnitine in the treatment of painful peripheral neuropathies in HIV+patients," *J. Peripher. Nerv. Syst.* 2(3):250-252 (1997).
Shor-Posner et al, "Neuroprotection in HIV-positive drug users: implications for antioxidant therapy," *J. Acquir. Immune Defic. Syndr.* 31 Suppl 2:S84-S88 (2002).
Simpson et al., "Neurologic manifestations of HIV infection," *Ann. Intern. Med.* 121(10):769-785 (1994). Review. Erratum in: *Ann. Intern. Med.* 122(4):317 (1995).
UF News, "UF Researcher Finds Vitamins and Exercise May Slow the Harmful Effects of Aging," http://www.napa.ufl.edu/2003news/vitamine.htm (2003).
Witschi et al., "The systemic availability of oral glutathione," *Eur. J. Clin. Pharmacol.* 43(6):667-669 (1992).
Ziegler et al., "Alpha-lipoic acid in the treatment of diabetic peripheral and cardiac autonomic neuropathy," *Diabetes* 46 Suppl 2:S62-S66 (1997).
Ziegler et al., "Alpha-lipoic acid in the treatment of diabetic polyneuropathy in Germany: current evidence from clinical trials," *Exp. Clin. Endocrinol. Diabetes* 107(7):421-430 (1999).
Hart A., Wilson A., Montovani C., et al., "Aceytl-L-carnitine: a pathogenesis based treatment for HIV-associated antiretroviral toxic neuropathy," *AIDS* 204;18:1549-1560 (2004).
Herzenberg L., De Rosa S., Dubs J., et al., "Glutathione deficiency is associated with impaired survival in HIV disease," *ProcNatlAcadSci USA*, 1997; 94:1967-1972.
McComsey G., Southwell H., Gripshover B., et al., "Effect of Antioxidants on Glucose Metabolism and Plasma Lipids in HIV-Infected Subjects with Lipoatrophy," *JAIDS* 2003;33:605-607.
Moretti S, Alesse E, Di Marzio L, et al. "Effect of L-carnitine on human immunodeficiency virus-1 infection-associated apoptosis: a pilot study," *Blood* 1998;91:3817-3824.

Total Daily Nutrient Dosages Per Two Packets

Five white capsules contain:

Vitamins

| | | | |
|---|---|---|---|
| Vitamin A (Beta Carotene) | 10,000 IU | Niacinamide | 30 mg |
| Vitamin A (Palmitate) | 4,000 IU | Calcium Pantothenate | 30 mg |
| Vit C (Calcium Ascorbates) | 900 mg | Choline (Citrate) | 60 mg |
| Bioflavinoid Complex | 150 mg | Inositol | 30 mg |
| Vitamin E (d-alpha Tocopheryl) | 400 IU | Folic Acid (Folacin) | 400 mcg |
| Vitamin B-1 (Thiamine HCl) | 30 mg | Biotin | 25 mcg |
| Vitamin B-2 (Riboflavin) | 30 mg | Vitamin D3 (Cholicalciferol) | 200 IU |
| Vitamin B-6 (Pyroxidine HCL) | 130 mg | Vitamin B12 (Methylcobalamin) | 1.25 mg |

Minerals

| | | | |
|---|---|---|---|
| Calcium (Citrate/Ascorbate) | 400 mg | Zinc (Picolinate) | 15 mg |
| Magnesium (Citrate) | 200 mg | Selenium (Picolinate) | 100 mcg |
| Iron (Picolinate) | 9 mg | Chromium (Picolinate) | 50 mcg |
| Iodine (K iodide) | 75 mcg | Molybdenum (Picolinate) | 150 mcg |
| Copper (Picolinate) | 1 mg | Boron (Picolinate) | 1 mg |
| Manganese (Picolinate) | 5 mg | Betaine HCL | 75 mg |
| Potassium (Citrate) | 50 mg | Glutamic Acid HCL | 50 mg |

Three colored capsules contain:

| | |
|---|---|
| Alpha Lipoic Acid | 200 mg |
| Acetyl L-Carnitine | 500 mg |
| N-Acetyl Cysteine | 600 mg |

Figure 1

Total Daily Nutrient Dosages Per Two Packets

Five white capsules contain:

Vitamins

| | | | |
|---|---|---|---|
| Vitamin A (Beta Carotene) | 20,000 IU | Niacinamide | 60 mg |
| Vitamin A (Palmitate) | 8,000 IU | Calcium Pantothenate | 60 mg |
| Vit C (Calcium Ascorbates) | 1,800 mg | Choline (Citrate) | 60 mg |
| Bioflavinoid Complex | 300 mg | Inositol | 60 mg |
| Vitamin E (d-alpha Tocopheryl) | 800 IU | Folic Acid (Folacin) | 800 mcg |
| Vitamin B-1 (Thiamine HCl) | 60 mg | Biotin | 50 mcg |
| Vitamin B-2 (Riboflavin) | 60 mg | Vitamin D3 (Cholicalciferol) | 400 IU |
| Vitamin B-6 (Pyroxidine HCL) | 260 mg | Vitamin B12 (Methylcobalamin) | 2.5 mg |

Minerals

| | | | |
|---|---|---|---|
| Calcium (Citrate/Ascorbate) | 800 mg | Zinc (Picolinate) | 30 mg |
| Magnesium (Citrate) | 400 mg | Selenium (Picolinate) | 200 mcg |
| Iron (Picolinate) | 18 mg | Chromium (Picolinate) | 100 mcg |
| Iodine (K iodide) | 150 mcg | Molybdenum (Picolinate) | 300 mcg |
| Copper (Picolinate) | 2 mg | Boron (Picolinate) | 2 mg |
| Manganese (Picolinate) | 10 mg | Betaine HCL | 150 mg |
| Potassium (Citrate) | 99 mg | Glutamic Acid HCL | 100 mg |

Three colored capsules contain:

| | |
|---|---|
| Alpha Lipoic Acid | 400 mg |
| Acetyl L-Carnitine | 1000 mg |
| N-Acetyl Cysteine | 1200 mg |

Figure 2

|  | Dosage/70 KG | UNITS | Dosage/Kg | UNITS |
|---|---|---|---|---|
| Beta Carotene | 20,000 | international units | 285.71 | international units |
| Vitamin A | 8,000 | international units | 114.29 | international units |
| Vitamin C | 600 | milligrams | 8.57 | milligrams |
| Vitamin D | 400 | international units | 5.71 | international units |
| Vitamin E | 800 | international units | 11.43 | international units |
| Vitamin B1 | 60 | milligrams | 0.86 | milligrams |
| Vitamin B2 | 60 | milligrams | 0.86 | milligrams |
| Vitamin B6 | 260 | milligrams | 3.71 | milligrams |
| Niacinamide | 60 | milligrams | 0.86 | milligrams |
| Folic acid | 800 | micrograms | 11.43 | micrograms |
| Vitamin B12 | 2.5 | milligrams | 0.04 | milligrams |
| Biotin | 50 | micrograms | 0.71 | micrograms |
| Inositol | 60 | milligrams | 0.86 | milligrams |
| Pantothenic acid | 60 | milligrams | 0.86 | milligrams |
| Potassium | 99 | milligrams | 1.41 | milligrams |
| Calcium | 800 | milligrams | 11.43 | milligrams |
| Iron | 18 | milligrams | 0.26 | milligrams |
| Iodine | 150 | micrograms | 2.14 | micrograms |
| Magnesium | 400 | milligrams | 5.71 | milligrams |
| Zinc | 30 | milligrams | 0.43 | milligrams |
| Selenium | 200 | micrograms | 2.86 | micrograms |
| Copper | 2 | milligrams | 0.03 | milligrams |
| Manganese | 10 | milligrams | 0.14 | milligrams |
| Chromium | 100 | micrograms | 1.43 | micrograms |
| Molybdenum | 300 | micrograms | 4.29 | micrograms |
| Choline | 60 | milligrams | 0.86 | milligrams |
| Glutamic acid | 100 | milligrams | 1.43 | milligrams |
| Boron | 2 | milligrams | 0.03 | milligrams |
| Betaine HCL | 150 | milligrams | 2.14 | milligrams |
| Bioflavinoid complex | 300 | milligrams | 4.29 | milligrams |
| Alpha lipoic Acid | 400 | milligrams | 5.71 | milligrams |
| Acetyl L-carnitine | 1000 | milligrams | 14.29 | milligrams |
| N-acetyl cysteine | 1200 | milligrams | 17.14 | milligrams |

*Effective concentrations of this formula can range from 25% to 200% of the per kilogram dosages listed to achieve the desired treatment effect.

Figure 3

NUTRIENT COMPOSITIONS AND METHODS FOR ENHANCED EFFECTIVENESS OF THE IMMUNE SYSTEM

This application is a continuation of U.S. application Ser. No. 13/117,811, filed May 27, 2011, which is a continuation of U.S. application Ser. No. 12/044,907, filed Mar. 7, 2008, issued as U.S. Pat. No. 7,951,847, which is a continuation of U.S. application Ser. No. 10/750,545, filed Dec. 31, 2003, now abandoned, the contents of which are incorporated herein by reference in their entirety.

This invention relates generally to promoting the healing process of physiological disorders or diseases and, more specifically to nutrient compositions that promote the effectiveness or efficiency of the immune system.

Physiological disorders and diseases affect millions of individuals each year. Severity of such pathological conditions can range from mild discomfort, to severe and permanent debilitating state, to a life-ending terminal disease. Treatments have continually strived to achieve cures that will restore an affected individual to a normal physiological state. For many disorders or diseases, medical treatments are limited to reduction in severity of symptoms or improvement in one's quality of living. Therefore, improvement in the efficacy of an available treatment continues to be a area of medical concern.

The diagnosis and treatment of human diseases similarly continues to be a major area of social concern. As long as there continues to be diseases that affect individuals there will be an effort to understand the cause of such diseases as well as efforts to diagnose and treat such diseases. Preservation of life and reducing the burden on society are two motivating factors that encourage the time and expenditure invested into scientific discovery and development processes. Applying the results of these scientific process to the medical field has led to surprising advancements in medicine which have improved both the quality of life and the life-span of affected individuals.

However significant in both scientific and medical contribution to their respective fields, the progression of advancements has been slow and painstaking, generally resulting from step-wise trial and error hypothesis-driven research. Moreover, with each advancement there can be cumulative progression in the overall scientific understanding of a problem but there is no guarantee that the threshold needed to translate a discovery into a practical medical application has been achieved. Additionally, with the achievement of all too many advancements comes the realization that the perceived final answer for a complete understanding of a particular physiological or biochemical process is, instead, just a beginning to a more complex process, which requires further dissection and understanding. Further complicating the progression of scientific advancements and their practical application can result from technical limitations in the available methodology.

In addition, even the most beneficial therapeutics available for a particular disorder or disease can result in undesirable side effects. For example, cancer chemotherapies and acquired immune deficiency syndrome (AIDS) treatments cause severe toxic effects due to their lack of specificity or to the occurrence of toxic by-product reactions. Additionally, many times an individual will become resistant to therapeutics during a treatment regime. Numerous other examples of undesirable side effects resulting from therapeutic treatment of, for example, immune-mediated diseases, heart disease, chronic fatigue syndrome, neurodegenerative diseases or an infectious disease also are prevalent and well known occurrences within the medical field.

The ability to reduce undesirable side effects while maintaining efficacy of a treatment remains an intense area of investigation. Predictability has been hampered in part because of the complexity of the human physiological system and the lack of a complete understanding of physiological mechanisms. For example, the advent of monoclonal antibodies and recombinant DNA technology, each having been hailed as technology that would revolutionize medicine and provide the ability to design highly specific therapeutics for diseases, has yielded less than promising results. Only some 30 years after the discovery of monoclonal antibodies are antibody therapeutics becoming available for therapeutic use. This long delay has resulted from the development of complementary technology that renders the antibodies less toxic to the recipient. Therefore, while beneficial in treating and controlling the impact of physiological disorders and diseases, advances in therapeutic medicines still fall short of providing the sought after cure or the ability to deliver a desired treatment regime to maintain a consistent improvement in quality of living.

Thus, there exists a need for compositions and methods that enhance efficacy of therapeutic treatments or provide desirable health benefits. The present invention satisfies this need and provides related advantages as well.

SUMMARY OF THE INVENTION

The invention provides a nutrient composition for augmenting immune strength or physiological detoxification. The nutrient composition consists of an optimal combination of an effective amount of at least one vitamin antioxidant, at least one mineral antioxidant and a highly saturable amount of at least three high potency antioxidants. The at least one vitamin antioxidant can be vitamin C, bioflavonoid complex, vitamin E, vitamin B6 or beta-carotene and the at least one mineral antioxidant can be zinc or selenium. The at least three high potency antioxidants can be alpha lipoic acid, acetyl L-carnitine, N-acetyl-cysteine, co-enzyme Q10 or glutathione. Also provided is a nutrient composition for augmenting immune strength or physiological detoxification that consists of an optimal combination of an effective amount of at least three vitamin antioxidants, at least two mineral antioxidants and a highly saturable amount of at least three high potency antioxidants. Further provided is a method of stimulating immune system function or a method of augmenting a therapeutic treatment of a disease. The method consists of administering to an individual a nutrient composition of the invention one or more times a day over a period of about 5-7 weeks, the immune system function being stimulated to result in an increase of CD4+ cells of at least about 15% compared to pre-administration levels. A method of stimulating a physiological detoxification function of an individual or a method of augmenting a therapeutic treatment of a disease is also provided. The method consists of administering to an individual a nutrient composition of the invention one or more times a day over a period of about 5-7 weeks, the physiological detoxification function being stimulated to result in a decrease of one or more free radical markers by about 20% compared to pre-administration levels.

BRIEF DESCRIPTION OF THE DRAWINGS

FIG. 1 shows an exemplary optimal combination of a nutrient composition and daily dosage for an individual weighing less than about 60 kg.

FIG. 2 shows an exemplary optimal combination of a nutrient composition and daily dosage for an individual weighing about 60 kg or more.

FIG. 3 shows the nutrient composition shown in FIG. 2 and daily dosages represented as the nutrient amount per kilogram of body weight for an individual weighing about 70 kg.

DETAILED DESCRIPTION OF THE INVENTION

This invention is directed to nutrient formulations that promote the effectiveness or efficiency of an immune system. The nutrient formulations also promote the effectiveness or efficiency of mitochondrial functions leading to enhanced energy production, detoxification functions of detoxifying organs and decreasing free radical generation or other oxidative processes. The nutrient formulations have the advantage in that they can be used in combination with other therapies to augment concurrent treatment or they can be used alone on healthy or diseased individuals to promote the health state or delay onset or severity of a disease.

In one embodiment, the invention is directed to nutrient formulations consisting of an optimal combination of about five antioxidants obtained from about three different categories of antioxidants. In a specific embodiment, the optimal combinations are formulated with a total of about 33 nutrients where there are 16 vitamin nutrients, 14 mineral nutrients and three high potency antioxidants. The nutrient formulation can be administered once or twice a day over a twelve week treatment in doses such as those shown in FIG. 3 to reduce the toxic effects of human immunodeficiency virus (HIV) therapeutics. This treatment can result in improvement of energy levels and pain scores as well as an increase of about 15% or greater in $CD4^+$ cell count compared to pretreatment levels.

In another embodiment, the optimal combinations of nutrients in the formulations of the invention can be used as an antidote to neutralize toxic effects resulting from HIV therapeutics. Several HIV therapeutics exhibit the adverse effect of inhibiting mitochondrial DNA polymerase gamma, which decreases mitochondrial function and increases oxidative stress. The optimal combinations prevent or reverse this inhibitory effect resulting in greater efficacy for the HIV therapeutics with less undesirable toxic side effects.

As used herein, the term "immune strength" is intended to mean an increase in the activity of an immune system function or an increase in the amount of a component of the immune system. Immune strength can include an increase in one, many or all functions of an immune system as well as an increase in the amount of one, many or all components of an immune system. Stimulation can occur, for example, through enhancement of an activity such as by the activation of a positive regulator or the repression of a negative regulator. Alternatively, stimulation can occur, for example, through suppression of an activity such as by the repression of a positive regulator or the activation of a negative repressor. These means of modulating immune system function as well as other means well known in the art are included within the meaning of the term as it is used herein. Activities or components of the immune system include those within any or all of the cellular, humoral or innate immune systems of an organism. An activity of an immune system includes those activities exhibited or mediated by cells or molecular components of these immune systems of an organism's immune system. The term "stimulating immune system function" as it is used herein is intended to be synonymous with the meaning of the term "immune strength."

As used herein, the term "physiological detoxification" is intended to mean a reduction of toxicity within a physiological environment. A physiological environment includes, for example, an organism, an organ, tissue, cell or cellular compartment. Physiological detoxification can occur, for example, directly or indirectly. A specific example of direct detoxification includes the inhibition of a poisonous substance or activity. Such poisonous substances can include, for example, reactants, products or by-products of biochemical or enzymatic reactions. Specific examples of indirect detoxification include causing an increase of physiological detoxification functions such as those that occur in the liver, boosting resistance to free radicals and other undesirable oxidative conditions.

As used herein, the term "optimal combination" when used in reference to immune strength is intended to mean a formulation of two or more nutrients each in an effective amount that together favorably stimulate immune system function. An optimal combination includes combinations of nutrients that together yield preferable immune stimulation results as well as combinations that produce more favorable immune strength results compared to other stimulatory formulations. An example of the former optimal combination includes a beneficial stimulation of immune system function compared to that which can be achieved with individual or combinations of nutrients. An example of the latter optimal combination includes stimulation of immune system function over that which can be obtained with individual or combinations of nutrients. The amount or degree of immune strength can be more favorable or the most favorable compared to a reference end point. Therefore, an optimal combination of nutrients includes a formulation of nutrients that either beneficially stimulates immune functions or enhances immune strength, or both, compared to results achievable with other nutrients or combinations of nutrients.

Cellular immunity activities include, for example, T cell functions such as effector and regulatory cell functions and can include enhancing or modulating the inflammatory response or augmenting the production of antibodies from B cells. Helper T cells prepare, for example, both antibody-mediated and cell-mediated effector cells for immune recognition and removal while suppressor T cell down regulate these responses. $CD4^+$ cells are a specific example of helper T cells that regulate both cellular and humoral effector cells through recognition of antigen in association with MHC Class II. Other activities of cellular immunity include the functions associated with, for example, natural killer cells, which recognize and destroy foreign cells on contact and cytotoxic T cells, or $CD8^+$ cells, which recognize and destroy pathogen infected host cells.

An activity of the humoral immune system includes, for example, those functions associated with B cells such as the production of antibodies while an activity of the innate immune system includes, for example, those functions associated with macrophages, neutrophils and eosinophils and other antibody-dependent cell cytotoxicity mediated events. Molecular components of the immune system that can be increased include, for example, cell signaling and complement mediated events. These activities as well as others are well known to those skilled in the art and can be found described in, for example, Kuby, *Immunology*, 3rd Edition, W.H. Freeman & Co., New York (1997) and in Paul, W. E., *Fundamental Immunology*, $3^{rd}$ Edition, Raven Press, New York (1989).

As used herein, the term "nutrient" is intended to mean both micronutrients and macronutrients that are required for biochemical and physiological processes of an animal. Micronutrients include organic compounds or chemical elements required in small amounts for biochemical and physiological processes. Such organic compounds and chemical elements include, for example, vitamins, minerals, antioxidants, cofactors, free radical scavengers or other biochemical compounds that are utilized in small amounts for the maintenance, regulation or function of biochemical and physiological processes.

The term "vitamin" as it is used herein, is intended to mean a micronutrient that acts generally in small amounts in the regulation of various metabolic processes but generally do not serve as an energy source or as a building unit. Vitamins are ordinarily ingested on a regular basis or stored in quantity in humans due to deficiencies in biosynthetic capacity. Specific examples of vitamin micronutrients include vitamins A, B, C, D and E.

The term "mineral" as it is used herein, is intended to mean a naturally occurring homogeneous or apparently homogeneous and generally solid crystalline chemical element or compound that results from inorganic processes of nature having a characteristic crystal structure and chemical composition. Specific examples of mineral and chemical element micronutrients include zinc, iron, iodine and boron.

The term "antioxidant" as it is used herein, is intended to mean a substance that opposes oxidation or inhibits reactions promoted by, for example, oxygen, peroxides or free radicals. Specific examples of antioxidant micronutrients include vitamin C, bioflavinoid complex, vitamin E, vitamin B6 and beta-carotene. Specific examples of cofactor micronutrients include vitamin B1, vitamin B2 and vitamin B6.

Macronutrients include organic compounds and chemical elements which are required in relatively large amounts for biochemical and physiological processes of an animal. Specific examples of macronutrients include, potassium, calcium and magnesium. Therefore, the term "nutrient" as it is used herein is intended to include vitamins, minerals, antioxidants, cofactors, free radical scavengers, elements or other biochemical compounds that are either or both micronutrient or macronutrient organic compounds and chemical elements as they are well known in the art. Specific examples of nutrients that are included in the optimal combinations of the invention are shown in FIGS. 1 and 2.

As used herein, the term "high potency" when used in reference to an antioxidant is intended to mean a non-vitamin or non-mineral antioxidant. The chemical or medicinal strength or the efficacy of such high potency antioxidants as they are found in the formulations of the invention can be, for example, greater in reducing oxidation, free radical destruction or chemical reactions induced by these chemical species compared to other antioxidants or compared to an amount of these same antioxidants as they are normally found in food. The chemical efficacy of the high potency antioxidants as they are used in the nutrient compositions of the invention can be due to, for example, greater molar amounts of antioxidants, enhanced antioxidant effectiveness resulting from cooperative combinations with other antioxidants or nutrients in the formulations of the invention. Therefore, high potency antioxidants as they are found in the nutrient compositions of the invention exhibit the ability or capacity to achieve more efficacious results. Specific examples of high potency antioxidants include alpha lipoic acid, acetyl L-carnitine, N-acetyl cysteine, coenzyme Q10 and glutathione.

As used herein, the term "effective amount" is intended to mean an amount of a nutrient that achieves stimulation of immune strength. When used in reference to immune strength of a nutrient contained within a formulation or combination of nutrients, the term is intended to refer to an amount that achieves immune strength of at least about a 15% increase in $CD4^+$ cells over an about 5-7 week course of administration. When used in reference to detoxification functions, the term is intended to refer to an amount that achieves a decrease in a free radical marker by at least about 20% over an about 5-7 week course of administration. Effective amounts of nutrients contained within the optimal combinations of the invention can be in excess of the recommended daily allowance (RDA), preferably in about 10-fold excess of the RDA and more preferably in about 20-fold excess of the RDA. Specific examples of effective amounts when used in the optimal combinations of the invention are show in FIGS. 1 and 2. FIG. 3 shows these exemplary effective amounts in the form of dosages per weight. Effective amounts can vary in range from these exemplary dosages by about 25% of the shown kilogram dosages up to and greater than about 200% of the shown kilogram dosages. Therefore, effective amounts for dosages of one or more of the nutrients shown in FIG. 3 can be, for example, 30, 40, 50, 60, 70, 80, 90, 110, 120, 130, 140, 150, 160, 170, 180, 190 or greater than 200% of the amounts per kilogram of body weight shown in FIG. 3. All percentages in between these values also are included within an effective amount of a nutrient of the invention. Other effective amounts can include, for example, amounts in excess of the RDA of about 11-, 12-, 13-, 14-, 15-, 16-, 17-, 18- or 19-fold as well as in excess of about 21-, 22-, 23-, 24-, 25- or 30-fold or more. Similarly, all values in between these exemplary fold-excess also are included within an effective amount of a nutrient of the invention. Effective amounts of high potency antioxidants also include, for example, ratios ranging from 1:1:1 to 1:4:6 in mg amounts of, for example, alpha-lipoic acid, acetyl L-carnitine and N-acetyl cysteine, respectively. Effective amounts other than those exemplified above also can be used in the nutrient formulations of the invention and will be known by those skilled in the art given the teachings and guidance provided herein.

As used herein, the term "highly saturable amount" when used in reference to a high potency antioxidant is intended to mean an amount of high potency antioxidant that maintains an excess of reduction potential during the course of treatment. Highly saturable amounts are in excess of the RDA, preferably in about 10-fold excess of the RDA and more preferably in about 20-fold excess of the RDA. Specific examples of highly saturable amounts for the high potency antioxidants are shown in FIGS. 1 and 2. FIG. 3 shows these exemplary effective amounts in the form of dosages per weight. Other effective amounts can include, for example, amounts in excess of the RDA of about 11-, 12-, 13-, 14-, 15-, 16-, 17-, 18- or 19-fold as well as in excess of about 21-, 22-, 23-, 24-, 25- or 30-fold or more. Effective amounts other than those exemplified above also can be used in the nutrient formulations of the invention and will be known by those skilled in the art given the teachings and guidance provided herein.

As used herein, the term "augmenting" is intended to mean facilitate or enhance a referenced activity, state or treatment. Facilitation or enhancement can occur, for example, by direct or indirect action of a nutrient formulation of the invention. When used in reference to immune strength or physiological detoxification, the term is intended to refer to improving the activity, performance or efficiency of an immune system or physiological detoxification functions of an organism. When used in reference to a therapeutic treatment, the term is intended to mean an enhancement of the beneficial effect of the treatment. Enhancement can occur by, for example, decreasing the oxidative state or improving the oxidative health of targeted or non-targeted cells. Enhancement also can occur by, for example, reducing the toxicity of the therapeutic treatment. These and other means of enhancing the therapeutic or beneficial effect of a treatment are included within the meaning of the term.

The invention provides a nutrient composition for augmenting immune strength or physiological detoxification. The nutrient composition consists of an optimal combination of an effective amount of at least one vitamin antioxidant, at least one mineral antioxidant and a highly saturable amount of at least three high potency antioxidants. The at least one vitamin antioxidant can be vitamin C, bioflavonoid complex, vitamin E, vitamin B6 or beta-carotene and the at least one mineral antioxidant can be zinc or selenium. The at least three high potency antioxidants can be alpha lipoic acid, acetyl L-carnitine, N-acetyl-cysteine, co-enzyme Q10 or glutathione.

The nutrient compositions of the invention are useful in a wide variety of applications to, for example, enhance immune function, increase energy states of cells and tissues, promote detoxification functions or to promote or maintain an overall healthy or balanced physiological environment. One advantage of the nutrient compositions of the invention is that they can simultaneously enhance the immune system strength and accelerate detoxification activities of a cell or organism. Further, the nutrient compositions of the invention can achieve unanticipated levels of immune system strength and accelerated detoxification because they provide multiple nutrients in supernormal amounts that together optimize the efficiency and effectiveness of enzyme systems, such as cellular enzyme systems. The nutrient compositions of the invention also can combine all, or substantially all, of the components in supernormal amounts to simultaneously optimize or enhance both primary and secondary enzyme systems. Supernormal amounts of nutrients in the composition formulations of the invention are beneficial because they can ensure that the activity or regulation of enzyme systems remains uncompromised.

The above and other characteristics of the nutrient compositions of the invention can be beneficially applied in conjunction with other therapeutic treatments to, for example, augment therapy, increase longevity or enhance the quality of life. Similarly, normal or healthy individuals also can benefit from use of the nutrient compositions to enhance or promote normal physiological functions. The nutrient compositions of the invention can supplement or augment intake requirements for vitamins, minerals, cofactors and antioxidants. Routine administration can ensure, for example, that the daily amounts required for normal physiological processes are met, as well as ensure an ample reservoir of such nutrients under physiological or metabolic stress when there is a need for increased nutrient amounts. Additionally, the nutrient compositions of the invention also can be taken based upon need, as when abnormal symptoms begin to occur for example, to defend against or retard the onset of a physiological disorder or disease.

The nutrient compositions of the invention are described herein primarily with reference to use in conjunction with a therapeutic treatment. However, it is understood that the beneficial effects afforded by a nutrient composition of the invention when used to promote or augment physiological mechanisms are equally applicable to promote or augment such physiological mechanisms in a normal individual or healthy state. Accordingly, the benefits and attributes accorded to the nutrient compositions when described in reference to enhancing a function or effect of a therapeutic treatment or a detoxification function are equally accorded to such functions or effects under normal or healthy states.

For example, the nutrient compositions of the invention can enhance the function and effect of antiretroviral drugs by elevating the mitochondrial energy output of all immune system cells. This elevation of mitochondrial energy output improves both mitochondrial number and function. In one study, described further below in Example I, the $CD4^+$ cell count for HIV patients taking a nutrient composition of the invention increased by an average of 26% over twelve weeks when compared to placebo. $CD4^+$ cells are an important marker of immune system strength. Increasing $CD4^+$ cell number or performance results in beneficial physiological consequences in either the healthy or diseased individual.

The nutrient compositions of the invention also can enhance the energy level and healing capacity for patients with an immune system dysfunction. Healing is a dynamic process that occurs within the individual. It is achieved when you go from your present level of health to one that is higher and more stable. It is an ongoing process. This enhancement in energy level and healing capacity can be attributed, for example, to the support of the mitochondria of cells throughout the body, particularly those of the immune system. Mitochondria are energy-producing organelles present in all mammalian cells and are important to maintain optimal cellular health, function and homeostasis of physiological systems.

The nutrient compositions of the invention also can prevent or reduce the toxicity from nucleoside reverse transcriptase inhibitor (nTRI) medications that are used to treat HIV infection. The term for this type of toxicity is "mitochondrial toxicity." The nutrient compositions of the invention contain, for example, vitamin, mineral and high potency antioxidants. Because mitochondria divide independently of cell division, and nRTI drugs are toxic to the mitochondria due to their inhibition of the enzyme mitochondrial DNA polymerase gamma, mitochondria are highly susceptible to drug-induced mitochondrial toxicity. Therapeutics that can induce mitochondrial toxicity include, for example, nTRI drugs as well as other potent medications or long-term administration regimes well known in the art. Mitochondrial toxicities are diverse in nature and reflect individual differences between a particular therapeutic, such as an individual nRTI, and the sensitivity of the target tissue. Specific mitochondrial toxicities can include, for example, hepatitis, anemia, peripheral neuropathy, pancreatitis, cardiomyopathy, lactic acidosis, radiation poisoning and fat redistribution. These mitochondrial toxicities as well as others well known to those skilled in the art are amenable to treatment with the nutrient compositions of the invention.

The nutrient compositions of the invention also can be used to enhance maintenance, performance or homeostasis of immunological or other physiological processes. The nutrient compositions described herein are formulated to contain optimal combinations of vitamin, mineral and antioxidant nutrients required in biochemical processes for normal physiological function. Administration of such multinutrient compositions ensures an adequate supply of needed nutrients to, for example, preclude nutrient availability as a rate limiting step. Moreover, ensuring an adequate supply facilitates, reduces or circumvents a lag phase when an immunological or other physiological response is invoked because, for example, the required nutrients are available or the cellular machinery is poised for any extra required activity. Accordingly, the nutrient compositions of the invention, when used either by an individual suffering from a physiological disorder or disease or a normal individual, can minimize undesirable burdens on biochemical or physiological cellular process, resulting in a benefit to some or all cellular or physiological systems of the individual.

Individuals that can benefit from administration of a nutrient composition of the invention include, for example, normal individuals, aging individuals as well as individuals infected or afflicted with one or more disorders or diseases such as an immune-mediated disease, cancer, heart disease, chronic fatigue syndrome, neurodegenerative diseases, infectious diseases, ischemic events, acute events or chronic events. Specific examples of such disorders or diseases include multiple sclerosis, lupus, rheumatoid arthritis, scleroderma, coronary artery disease, atherosclerotic vessel disease, Madalung's disease, neoplastic conditions, solid tumor malignancies, non-solid malignancies, Alzheimer's disease, Parkinson's disease, dementia, infectious hepatitis, toxic hepatitis, drug-induced hepatitis, herpes, human immunodeficiency virus (HIV) infection, acquired immunodeficiency syndrome (AIDS), stroke, radiation poisoning, toxic drug exposure or oxidative stress occurring as part of the normal aging process. Neurodegenerative forms of dementia include, for example, deteriorated mentality such as that observed with ischemic events, drug abuse, alcohol abuse or HIV/AIDS. Numerous other physiological disorders or diseases also are applicable for treatment with the nutrient compositions of the invention. Given the teachings and guidance provided herein, those skilled in the art will know, or can determine, such other abnormal physiological conditions applicable for treatment with the nutrient compositions of the invention.

The nutrient compositions of the invention can consist of a multinutrient formulation containing an optimal combination of vitamin, mineral and high potency antioxidants. The nutrient compositions of the invention alternatively can consist of an optimal combination of vitamin antioxidants, of mineral antioxidants or of high potency antioxidants. The nutrient compositions also can consist of an optimal combination of vitamin and mineral antioxidants, vitamin and high potency antioxidants or mineral and high potency antioxidants. The nutrient compositions similarly can consist of various other combinations of these antioxidants and can contain, for example, one, two, three, four or five or more different antioxidants. Antioxidants are beneficial to physiological processes because they augment immune strength or physiological detoxification functions within the cells or tissues of an individual. Moreover, multinutrient combinations are beneficial physiologically because of their interdependence in a variety of cellular and physiological process. For example, mammalian mitochondria are interdependent on multiple nutrients for healthful and efficient functioning. Ascorbate (vitamin C), alpha-tocopherol (vitamin E), alpha-lipoic acid, and glutathione (such as that derived from N-acetyl cysteine) are dependent upon each other to replenish their lower valence, bio-active moieties subsequent to oxidation by free radicals. Supplementing one or less than all of these interdependent nutrients can result in a loss of biochemical efficiency if the goal is to promote improved functioning of, for example, a dysfunctional Kreb's cycle or electron transport system. Other uses and beneficial effects of the nutrient compositions of the invention for augmenting immune strength or physiological detoxifications are described further below with reference to the methods of the invention.

Antioxidants function in a wide variety of physiological processes, including those described above and below as well as other process well known by those skilled in the art. Administration of multinutrient antioxidant formulations can improve the functions dependent on such antioxidants as well as improve the functions dependent on the interplay of antioxidants and of antioxidants with other nutrients such as vitamins and minerals. Optimal combinations of nutrients in the compositions of the invention include amounts or types of nutrients that together support the interdependent roles of two or more nutrients. A specific example of such interdependence is described above with reference to replenishing reduced molecular states of nutrients in the Kreb's cycle or electron transport chain. Other optimal combinations that support interdependence include, for example, the ability of Vitamin C (Ascorbate) to regenerate native Vitamin E (tocopherol) from its oxidized state as well as alpha lipoic acid to regenerate native ascorbate from its oxidized state.

Vitamin antioxidants that can be selected for inclusion in a nutrient composition of the invention as an optimal combination include, for example, vitamin C, bioflavinoid complex, vitamin E, vitamin B6 or beta-carotene. One or more of these or other vitamin antioxidants well known in the art can be included in a nutrient composition of the invention.

Vitamin C, or ascorbic acid or ascorbate, is a strong reducing agent that can be reversibly oxidized to dehydroascorbic acid. The term vitamin C, as it is used herein, is intended to include any of several enolic lactones of keto aldonic acids that are stereoisomers of ascorbic acid. As described above, vitamin C functions in, for example, the Kreb's cycle and a deficiency can lead to scurvy. Vitamin C also functions in building and maintaining bone matrix, cartilage, dentin, collagen, and connective tissue in general. Furthermore, Vitamin C participates in resistance to infection by the immune system and proper adrenal gland function in reaction or resistance to stress.

Bioflavinoid complex, or vitamin P, includes the substances rutin, citrin, hesperidin, and quercitin. These substances exhibit reducing and chelating properties and can be required for the proper function of minute blood vessels. They also play a role in modulating the inflammatory response, particularly of mast cells.

Vitamin E, or d-alpha tocopherol, is a fat-soluble tocopherol vitamin with powerful antioxidant properties. Vitamin E also plays a role in protecting cellular membrane fatty acids from oxidative damage. It is nutritionally required for mammals in which its absence is associated with infertility, muscular dystrophy, or abnormalities in the vascular system. The term vitamin E, as it is used herein, is intended to include, any of the structurally similar chemical compounds found within the tocopherol family of organic compounds.

Vitamin B6, or pyroxidine HCl or pyridoxine, is a component of the vitamin B complex and plays a role in the proper formation and health of red blood cells and blood vessels, nerve function, gums and teeth. Vitamin B6 also is involved in the amino acid metabolism. Although not generally considered to be an antioxidant, vitamin B6 does exhibit antioxidant properties.

Beta-carotene is a vitamin antioxidant that also is convertible to vitamin A in the liver of animals. This class of nutrients includes all those defined by the term "retinoids" and includes those described as retinols. Since Vitamin A is only found in animal foods, beta-carotene provides about two thirds of the daily intake of retinoids in humans. Beta-carotene is converted to Vitamin A in both the gastrointestinal tract and the liver. Vitamin A is used by the body to enhance retinal function and night vision and also plays a role in the formation and maintenance of healthy epithelial tissue, which forms the body's primary barrier to infection.

Mineral antioxidants that can be selected for inclusion in a nutrient composition of the invention as an optimal combination include, for example, zinc or selenium. Either or both of these minerals as well as other vitamin antioxidants well known in the art can be included in a nutrient composition of the invention.

Zinc, taken in the form of picolinate, carbonate, ascorbate, or complexed to a chelated amino acid, for example, is one mineral exhibiting antioxidant activity. Zinc also is utilized for the metabolic activity of about 200 or more enzymes and is considered important for cell division and the synthesis of DNA and polypeptides. Zinc deficiency contributes to growth retardation and even mild deficiency may limit growth in otherwise healthy children. Zinc functions, for example, in energy metabolism as part of the lactate dehydrogenase enzyme system. Zinc also participates in immune function, as evidenced by its role in promoting enhanced would healing, and serves as an antioxidant, such as part of the superoxide dismutase enzyme system.

Selenium, taken in the form of picolinate, carbonate, ascorbate, or complexed to a chelated amino acid for example, is another mineral having antioxidant activity. Selenium is an important component of the active sites of, for example, the enzymes glutathione peroxidase, iodothyronine 5'-deiodinase and mammalian thioredoxin reductase. It is also present in several other mammalian selenoproteins. Both glutathione peroxidase and thioredoxin reductase catalyze reactions involved in the protection of cellular components against oxidative and free radical damage. Therefore, selenium as well as zinc and other nutrients within the compositions of the invention augment the activity of enzymes within one or more antioxidant enzyme systems of an individual. Selenium also plays a role as a mammalian cell's second line of defense against damaging cell peroxides. It performs this role as an integral part of the glutathione peroxidase enzyme system.

High potency antioxidants that can be selected for inclusion in a nutrient composition of the invention as an optimal combination include three or more of, for example, alpha lipoic acid, acetyl L-carnitine, N-acetyl-cysteine, co-enzyme Q10 or glutathione.

Alpha lipoic acid is a potent antioxidant found, for example, in the mitochondria. It acts as a coenzyme in the alpha-keto-dehydrogenase enzyme complex of the Kreb's cycle to facilitate aerobic respiration as well as participates in the metabolic pathways which regenerate de novo levels of ascorbate, alpha-tocopherol, and glutathione. Alpha lipoic acid also functions as a potent free radical scavenger. In addition to these antioxidant activities, alpha-lipoic acid also can, for example, inhibit NF-kappa B activation, HIV replication in cell cultures and reduce the severity of peripheral neuropathy in diabetes mellitus patients (Packer et al., *Mol. Aspects of Med.* 14:229-239 (1993); Baur et al., *Klin. Wochenschr.* 69:722-724 (1991)). Alpha lipoic acid also may to increase the number of CD4$^+$ cells and the CD4:CD8 ratio in HIV-infected patients (Fuchs et al., *Arzneimittelforschung* 43:1359-1362 (1993)).

Acetyl L-carnitine is similarly a nutrient with potent antioxidant activity because it supports antioxidant activity under a diverse set of conditions. The acetyl moiety of the amino acid carnitine regulates fatty acid transport across the mitochondrial membrane. It enhances mitochondrial function and energy production utilized in antioxidant activities by providing additional fuel stores during times of oxidative stress. It also functions to provide mitochondria with a fuel source that enhances its ability to produce energy under anaerobic conditions. Anaerobic metabolism can occur, for example, when the electron transport chain is dysregulated due to a depletion of mitochondrial DNA. In addition to the antioxidant and other energy functions of acetyl L-carnitine, this nutrient also can, for example, reduce symptoms of zidovudine (AZT)-induced mitochondrial myopathy (Campos et al., *Muscle Nerve.* 16:150-153 (1993); Dalakas et al., *Ann. Neurol.* 35:482-487 (1994)), or peripheral neuropathy in diabetes mellitus or HIV infection (Famularo et al., *J. Peripher. Nerv. Syst.* 3:227-29 (1998)). Acetyl L-carnitine deficiency has also been shown to be present in HIV-infected individuals diagnosed with peripheral neuropathy (Famularo e al., *AIDS* 11:185 (1997)).

N-Acetyl Cysteine (NAC) is another nutrient with potent antioxidant activity. The acetyl moiety of the amino acid cysteine is a prevalent bioavailable oral source of glutathione. Glutathione is a potent antioxidant and component of the glutathione peroxidase enzyme system. In contrast, glutathione deficiency can be associated, for example, with a poor prognosis in HIV disease (Aukrust et al., *Nutrition* 15:165-167 (1999); De Quay et al., *AIDS* 6:815-819 (1992)), and that the HIV Tat protein or nRTI medications may contribute to a reduction of glutathione levels in HIV-infected cells (Choi et al., *J. Biol. Chem.* 275:3693-3698 (2000)).

Co-enzyme Q10 (ubiquinone) is a further nutrient with potent antioxidant activity. This antioxidant functions as an intermediary in the electron transport system in the mitochondria of every cell and adequate amounts of this nutrient are needed for optimal production of ATP. Coenzyme Q10 also functions in the mitochondria as an intracellular antioxidant and adequate levels are needed for the healthful functioning of all human tissues and organs. Tissues, organs, and systems that are the most metabolically active are more dependent on adequate Coenzyme Q10 levels. Such metabolically active tissues include, for example, heart, liver, immune system and gastric mucosa.

Any of the nutrient antioxidants describe above as well as others well known in the art can be included in a nutrient composition of the invention. Additionally, other nutrients that function, for example, in one or more of the antioxidant enzyme systems described above or others well known in the art also can be included or substituted for one or more vitamin, mineral or high potency antioxidants included in a nutrient composition described herein. For example, the nutrients selenium, alpha lipoic acid and NAC participate in the glutathione peroxidase enzyme system or function to regenerate reduced glutathione and result, for example, in the protection of cellular components against oxidative and free radical damage. Those skilled in the art will understand that glutathione can be used, for example, as a functional equivalent for these antioxidants and be substituted for a vitamin, mineral or high potency antioxidant to achieve the same or similar results. Various other antioxidant substitutions as functional equivalents also can be included in the nutrient compositions of the invention. Given the teachings and guidance provided herein, those skilled in the art will know, or can determine, which other antioxidants can be substituted without loosing physiological effect or activity.

The nutrient compositions consist of at least one vitamin antioxidant, at least one mineral antioxidant and at least three high potency antioxidants. For example, one nutrient composition can contain an effective amount of vitamin C as a vitamin antioxidant, zinc as a mineral antioxidant and alpha lipoic acid, acetyl L-carnitine and NAC as the three high potency antioxidants. Another nutrient composition can contain an effective amount of, for example, bioflavinoid complex as a vitamin antioxidant, zinc as a mineral antioxidant and alpha lipoic acid, acetyl L-carnitine and NAC as the three high potency antioxidants. Further, an additional nutrient composition of the invention can contain an effective amount of, for example, vitamin E as a vitamin antioxidant, zinc as a mineral antioxidant and alpha lipoic acid, acetyl L-carnitine and NAC as the three high potency antioxidants. Similarly, vitamin B6 or beta-carotene also can be substituted for the vitamin antioxidant component of the nutrient composition. In like manner, each of the exemplary vitamin antioxidants can be combined with selenium in substitution for zinc as the mineral antioxidant, while still containing alpha lipoic acid, acetyl L-carnitine and NAC as the three high potency antioxidants. Further, co-enzyme Q10 or glutathione or both can be substituted for one or more of the high potency antioxidants alpha lipoic acid, acetyl L-carnitine or NAC. All of the various combinations of the above vitamin, mineral and high potency antioxidants are also included herein as a nutrient composition of the invention.

The nutrient compositions also can contain, for example, two or more vitamin antioxidants or two or more mineral antioxidants or combinations of two or more vitamin antioxidants and at least one mineral antioxidant or at least one vitamin antioxidant and two or more mineral antioxidants. Nutrient compositions containing more than one vitamin or mineral antioxidant also will contain at least three high potency antioxidants. For example, in addition to containing alpha lipoic acid, acetyl L-carnitine and NAC, or substitutable equivalents such as glutathione or co-enzyme Q10, a nutrient composition can contain two or more of vitamin C, bioflavinoid complex, vitamin E, vitamin B6 or beta-carotene as well as zinc, selenium or both. All of the various combinations of these vitamin, mineral and high potency antioxidants are included herein as a nutrient composition of the invention. An exemplary nutrient composition containing more than one vitamin and more than one mineral antioxidant can be, for example, a combination of effective amounts of vitamin C, bioflavinoid complex, vitamin E, zinc, selenium, alpha lipoic acid, acetyl L-carnitine and NAC. Given the teachings and guidance provided herein, those skilled in the art will know, or can determine, what other combinations of at least one vitamin antioxidant, at least one mineral antioxidant and at least three high potency antioxidants can be included in a nutrient composition of the invention that will maintain activity for augmenting immune strength and detoxification functions of a physiological system.

The nutrient compositions of the invention also can contain one or more additional vitamins, minerals, vitamin or mineral antioxidants or high potency antioxidants or any combination thereof. Vitamins and minerals can be additionally included to further promote the immune strength or detoxification functions of the nutrient compositions of the invention. Effective amounts of such additional vitamins or minerals or additional antioxidants, including high potency antioxidants, will provide additional reservoirs of nutrients required by biochemical and physiological process to perform their respective functions under either or both normal or stressful conditions. As with the antioxidants described previously, inclusion of effective amounts of one or more vitamins or minerals can result in optimal performance of physiological processes due to the interplay or interdependency of nutrients in biochemical reactions.

Additional vitamins or minerals that can be included in the nutrient compositions of the invention include those shown in FIG. 1 or 2 other than the antioxidants described previously. For example, one or more nutrients from the vitamin category can be additionally included. Similarly, one or more nutrients from the mineral category can be additionally included. Alternatively, one or more nutrients from both the vitamin and the mineral categories can be additionally included in the antioxidant nutrient compositions of the invention. Therefore, the nutrient compositions can include any one or more, as well as all of the various combinations of the following vitamins or minerals: beta-carotene, vitamin A, vitamin B1, vitamin B2, vitamin B6, niacinamide, calcium panthothenate, choline, inositol, folic acid, biotin, vitamin D3, vitamin B12, calcium, magnesium, iron, iodine, copper, manganese, potassium, chromium, molybdenum, boron, betaine, glutamic acid.

The above vitamins and minerals as well as others known in the art function in a wide variety of metabolic, biochemical or physiological processes. As such, they are useful to promote efficiency of their respective processes as well as augment the functioning of the antioxidant nutrients of the invention. Accordingly, when included in a nutrient composition of the invention, these vitamins or minerals similarly can augment immune strength or detoxification functions including, for example, reducing mitochondrial oxidative stress and/or oxidative damage. Exemplary functions and activities of these vitamins and minerals are described further below and can be found described in, for example, Williams, B. R., *Nutrition and Diet Therapy* (6th Ed), Times Mirror/Mosby Collage Publishing, St. Louis, Mo. (1989).

For example, thiamine (vitamin B1) is a water-soluble, B-complex vitamin needed to metabolize proteins, carbohydrates, and fats. It is used as a cofactor in numerous enzymes, enhances nervous system health, and is used by cells for ATP production via the Kreb's cycle.

Riboflavin (vitamin B2) is a water-soluble, B-complex vitamin that is a constituent in several enzymes known as flavoproteins. Two such riboflavin enzymes, flavin mononucleotide (FMN) and flavin-adenine dinucleotide (FAD), operate in the respiratory chain of cellular energy metabolism to produce ATP.

Pyridoxine (vitamin B6) is a water-soluble, B-complex vitamin that, in its active form pyridoxalphosphate ($B6-PO_4$), is a coenzyme involved in many types of transamination and decarboxylation reactions occurring in amino acid, carbohydrate and fat metabolism. Vitamin B6 also is a cofactor in immune system functioning.

Niacinamide (a form of niacin) is a water-soluble, B-complex vitamin that is a constituent of the cellular enzymes utilized in energy metabolism and the production of ATP. Two niacin coenzymes that operate in these reactions are nicotinamide-adenine dinucleotide (NAD) and nicotin-amide-adenine dinucleotide phosphate (NADP).

Pantothenic acid is a water-soluble B-complex vitamin that globally participates in metabolic processes due to its ability to promote acetylation.

Choline, folic acid and vitamin B12 are nutritional factors involved in transmethylation reactions. Choline is a component of two phospholipids compounds made by the body: lecithin and sphingomyelin.

Inositol can function as an antioxidant by chelating divalent cations such as copper and iron. Chelation of divalent cations can prevent the formation of reactive oxygen species (ROS) responsible for cell injury and carcinogenesis.

Folic acid acts as a coenzyme which transfers single carbon units for attachment in many conversion reactions such as in the formation of hemoglobin. Folic acid deficiency can cause anemia.

Biotin functions as a coenzyme with specific cell enzymes involved in the process of carboxylation.

Vitamin D3 participates in the regulation of calcium and magnesium metabolism and in the synthesis of bone.

Vitamin B12 is needed for the production of red blood cells and healthy nervous system functioning.

Calcium is present in large amounts in the human body and is needed, for example, for structural integrity, blood clotting and nerve cell functioning.

Magnesium is needed for healthy intracellular metabolism of macromolecules such as carbohydrates and protein. A magnesium-ATP complex is the form of ATP used as a substrate in many biochemical reactions.

Iron is utilized for the production of the hemoglobin molecule of red blood cells.

Iodine functions as a precursor to the synthesis of thyroid hormone which controls the body's basal metabolic rate.

Copper is associated with iron in several metabolic reactions including those involved in energy production and the formation of hemoglobin.

Manganese, found in concentrated amounts in the mitochondria, functions as a catalytic component of several energy-producing enzyme systems.

Intracellular potassium helps to balance the osmotic pressure of cells by balancing extracellular sodium.

Chromium is a component of the organic complex glucose tolerance factor (GTF), which potentiates the action of insulin by facilitating the binding of insulin to the cell membrane.

Molybdenum functions as a catalytic component of several enzyme systems necessary for healthy metabolism.

Boron is a trace mineral that functions along with calcium and magnesium in formation of bone.

Glutamine (glutamic acid) is a prevalent amino acid in the bloodstream and a readily utilized source of energy for muscle cells and the intestinal mucosal lining.

Betaine hydrochloride is an acidic compound that facilitates the absorption of other nutrients in the compositions of the invention.

The nutrient compositions also can include all of the above additional vitamins and minerals together with all of the vitamin, mineral and high potency antioxidants described previously or any combination of at least one vitamin antioxidant, one mineral antioxidant and at least three high potency antioxidants. As with the antioxidants described previously, other vitamins or minerals well known in the art can similarly be included or substituted in the nutrient compositions of the invention.

Optimal combinations of the above and below described nutrient compositions include each nutrient in an effective amount. Similarly, the combination of nutrients together yield an effective amount for a total effect on stimulation of immune strength. Effective amounts of nutrients in the formulations of the invention include amounts of nutrients higher than those suggested by the U.S. Food and Drug Administration as the recommended daily allowances (RDA). The purpose of the RDA for vitamin and mineral intake is to promote normal health and eliminate nutrient deficiency diseases in otherwise healthy adults. The effective amounts described herein achieve this purpose because on their inclusion in a optimal combination in amounts in excess of the RDA. The effective amounts described herein also provide the benefit of producing an available reservoir for access under stress such as a diseased or pathological condition. Effective amounts of the nutrient compositions additionally poise cellular, biochemical and physiological processes for action because there reduce physiological burdens under depleted conditions. Therefore, by utilizing effective amounts above the RDA, the nutrient compositions are capable of augmenting immune strength or physiological detoxification functions as well as capable of preventing or reversing drug-induced toxicities. Preventing includes delaying the onset of a physiological disorder as well as reducing the severity of such disorders and diseases.

Effective amounts of the nutrient compositions of the invention include, for example, those amounts shown in FIGS. 1 and 2 and the dosages shown in FIG. 3. Additionally, a effective amount of co-enzyme Q10 can range, for example, from about 30-300 mg per day for an individual weighing about 70 kg. Glutathione dosages can range, for example, from about 100 mg/day to about 600 mg/day for an individual weighing about 70 kg. Such effective amounts are higher than the RDA for each nutrient listed as well as for all nutrients contained within an optimal combination of the invention. Effective amounts can vary depending on the need or availability of a nutrient and include, for example, a dosage ranging from about 25% to about 200% of those amounts per body weight listed in FIG. 3. Effective amounts higher and lower similarly can be employed in the optimal combinations of nutrients of the invention so long as they are in excess of the RDA or in excess of nutritional requirements under a particular physiological condition.

Effective amounts also can be defined as ratios of for example, antioxidants or high potency antioxidants. For example, effective amounts for the high potency antioxidants alpha lipoic acid, acetyl L-carnitine and NAC can include daily amounts of about 200 mg, 500 mg and 600 mg, respectively, for an individual weighing less than about 70 kg. Similarly, for an individual weighing about 70 kg or more, an effective amount can include daily intake of about twice these levels. Dosages include amounts per kilogram of body weight of about 5.71 mg, 14.29 mg and 17.14 mg, respectively, and can range from about 25% to about 200% of these dosages. Whether expressed as amounts or dosages per body weight, the high potency antioxidants are included in an optimal combination of the invention in a ratio ranging from about 1:1:1 to about 1:4:6, respectively. All values in between these ratios are similarly included as an effective amount for an optimal combination of the three high potency antioxidants alpha lipoic acid, acetyl L-carnitine and NAC, respectively, as well as functional equivalents thereof. Given the teachings and guidance provided herein, those skilled in the art will know, or can determine, the actual amounts, dosages or ratios other than those described above and exemplified in FIGS. 1-3 and in Table 2, that will augment immune strength or detoxification functions of a physiological process.

Efficacy of the nutrient compositions of the invention, including cooperative interactions between physiological processes, promotion of immune strength or detoxification functions, correlates with purity level of the nutrients within an optimal combination of the invention. Higher the purity levels yield greater activity and consequently can allow a reduction in the amount included in one or more administrations. Nutrient compositions having a purity level adequate for human ingestion is sufficient for augmentation of immune strength or detoxification functions.

The nutrients of the invention and optimal combinations in the compositions of the invention can have a purity level greater than about 90%, preferably greater than about 95% and more preferably greater than about 98%. Purity levels greater than about 98% percent can also have a purity of about 99% or greater as determined, for example, by total weight of the nutrient composition. These higher purity levels can be obtained by, for example, methods well known in the art. Additionally, purity levels greater than about 98% and particularly greater than about 99% by total weight can be obtained by omitting fillers, binders or lubricants such as stearates or palmitates. Additionally, other substances which are known in the art to inhibit, or known to possibly inhibit, the absorption, bioavailability or tolerance of compounds in individuals also can be excluded from the formulations to achieve greater than about 98-99% purity without compromising the activity of the nutrient compositions of the invention. However, it should be understood that such fillers, binders, lubricants or other substances also can be included in the nutrient compositions of the invention when, for example, it is desirable or an optimal efficacy is not needed to achieve a particular result. Given the teachings and guidance provided herein, those skilled in the art will know whether to utilize nutrient compositions less than the purity levels described above or to include additional substances in a formulation. Accordingly, various formulations well known in the art for packaging and administration of nutrients or other administrable chemical compounds can be utilized in conjunction with the nutrient compositions of the invention.

Nutrients for use in the formulations of the invention can be obtained from any of various sources known to those skilled in the art. For example, individual nutrients or optimal combinations meeting the amounts or dosages exemplified herein can be produced by a commercial manufacturer. An exemplary commercial manufacturer is Thorne Research (Dover Id., and which can be found at the URL thorne.com). Additionally, nutrients of the invention can be purified biochemically or synthesized chemically using methods well known to those skilled in the art.

Therefore, the invention also provides a nutrient composition for augmenting immune strength or physiological detoxification that consists of an optimal combination of an effective amount of at least three vitamin antioxidants, at least two mineral antioxidants and a highly saturable amount of at least three high potency antioxidants. The at least three vitamin antioxidants can be three vitamins selected from vitamin C, bioflavonoid complex, vitamin E, vitamin B6 or beta-carotene. The at least two mineral antioxidants can be zinc and selenium and the at least three high potency antioxidants can be three antioxidants selected from alpha lipoic acid, acetyl L-carnitine, N-acetyl-cysteine, co-enzyme Q10 or glutathione. Purity levels of the nutrient compositions can be 99% or greater by total weight. Further provided is a nutrient composition for augmenting immune strength or physiological detoxification that consists of an optimal combination of an effective amount of vitamin C, bioflavonoid complex, vitamin E, zinc, selenium, alpha lipoic acid, acetyl L-carnitine and N-acetyl-cysteine.

The invention additionally provides a method of stimulating immune system function. The method consists of administering to an individual a nutrient composition of the invention one or more times a day over a period of about 5-7 weeks, the immune system function being stimulated to result in an increase of $CD4^+$ cells of at least about 15% compared to pre-administration levels.

A method of stimulating a physiological detoxification function of an individual is also provided. The method consists of administering to an individual a nutrient composition of the invention one or more times a day over a period of about 5-7 weeks, the physiological detoxification function being stimulated to result in a decrease of one or more free radical markers by about 20% compared to pre-administration levels.

The antioxidant nutrients compositions of the invention can be used alone or in combination with additional vitamin or mineral nutrients to augment immune strength or detoxification functions of physiological processes. In addition to promoting specific physiological processes such as energy production, detoxification functions of cells and tissues, reduction in mitochondrial oxidative stress or a reduction in oxidative damage, the nutrient compositions of the invention exhibit measurable differences in indicators of immune system strength. For example, routine intake of a nutrient composition of the invention can result in a significant increase in the amount of $CD4^+$ cells within the immune system. Because $CD4^+$ cells are effector lymphocytes that promote and regulate other immune system cells, an increase in these cells also can result in enhanced function of the entire immune system. Therefore, routine intake of a nutrient composition of the invention also can result in increased amounts or performance of a wide variety of other immune system cells. Such immune system cells can be derived from the cellular, humoral or innate immunity components of the immune system and cells can include, for example, other helper T cells, natural killer cells, cytotoxic T cells, B cells, macrophages, neutrophils, eosinophils or other cells participating in antibody-dependent cell cytotoxicity. The levels or performance of immune system cells well known in the art other than those described above also can be enhanced with the nutrient compositions of the invention.

With reference to the specific example of $CD4^+$ cells, the nutrient compositions can result in an increase in $CD4^+$ cells by at least about 15% compared to $CD4^+$ cell levels or percentages prior to administration. Increases of $CD4^+$ cells substantially greater than about 15% compared to pre-administration levels also can be obtained as an indicator of immune strength. For example, administration of the nutrient compositions can result in a $CD4^+$ cells increase greater than about 25%, 30%, 35% or 40% or greater compared to pre-administration levels. As a measure of immune strength, higher levels or greater percentages of increase in $CD4^+$ cells indicates a commensurate increase in immune system strength. Such immune strength includes, for example, increases in immune system function, performance, efficiency or capacity as well as combinations thereof. Immune system cells other than $CD4^+$ cells also can be increased by comparable amounts and in approximate proportion to their normal physiological distribution within the an immune system. Additionally, augmenting immune strength also can occur by ensuring sustaining amounts of nutrients for optimal performance. The nutrient compositions of the invention achieve such sustaining amounts.

In addition to promoting immune strength, detoxification functions, reduced mitochondrial oxidative stress or reduced oxidative damage as well as other physiological process described herein, the nutrient compositions of the invention also exhibit measurable differences in indicators of physiological detoxification functions. For example, routine intake of a nutrient composition of the invention can result in a significant decrease in free radical markers. Reduction of free radical markers indicates a commensurate and proportional reduction in deleterious free oxygen species. Because free oxygen species are reduced, the detoxifying functions of cells and organelles are available to efficiently scavenger nascent free radicals and can result in an enhancement of the effectiveness or efficiency of immune strength, energy producing process or further detoxification functions. Therefore, routine intake of a nutrient composition of the invention also can result in increased performance or efficiency of a wide variety biochemical reactions or physiological processes. Accordingly, the performance or efficiency of detoxification functions well known to those skilled in the art other than those described herein also can be enhanced with a nutrient composition of the invention.

Particular clinical or laboratory free radical markers include, for example, plasma malondialdehyde (MDA), plasma lipid peroxides, reduced lipid peroxidation or plasma levels of glutathione (GSH). Methods for measuring these and other free radical markers are well know in the art. For example, diagnostic levels of MDA can be determined by high-performance-liquid-chromatography (HPLC) as well as other chromatographic methods well known in the art. Levels of reduced lipid peroxidation can be determined by, for example, breath pentane output. The above markers and their use as indicators of free oxygen species levels can be found described in, for example, Allard et al., *AIDS* 12:1653-1659 (1998). Various other indicators of free oxygen species well known in the art similarly can be utilized as a detoxification marker of the invention.

Exemplary detoxification functions augmented by a nutrient composition of the invention include detoxification processes of the liver, enhancement of hepatocyte functions, enhancement of energy production or increased efficiency of toxin processing due to a decrease in free radical buildup, for example. Additionally, detoxification functions utilized for reducing the severity of drug-induced toxicities such as nRTI-induced mitochondrial toxicity as well as others well known in the art also are augmented by a nutrient composition of the invention. These and other detoxification functions are exemplified further below.

The nutrient compositions of the invention can result in a decrease of one or more free radical markers by about 20% compared to the same marker prior to administration. Decreases in free radical markers substantially greater than about 20% compared to pre-administration levels also can be obtained as an indicator of detoxification function. For example, administration of the nutrient compositions can result in a free radical marker decrease of about 25%, 30%, 35%, 40%, 45% or 50% or greater compared to pre-administration levels. As a measure of detoxification function, reduced levels or a greater percent reduction in one or more free radical markers indicates a commensurate increase in one or more detoxification functions including, for example, increases in detoxification performance, efficiency or capacity as well as combinations thereof. Increased detoxification function includes, for example, increases in energy state and resources. As with augmenting immune strength, increasing detoxification functions also can occur by ensuring sustaining amounts of nutrients for optimal performance under normal or diseased conditions.

The nutrient compositions of the invention can be administered over both short and long periods of time. Effectiveness of the nutrient compositions is linked, for example, to availability of the nutrient components of the formulations. Accordingly, administration regimes can vary significantly so long as in vivo levels of the nutrients are maintained at substantially the same or similar levels as those achieved by the effective amounts provided herein for oral administration. Such levels are sufficient to maintain sustainable amounts in excess for optimal or enhanced performance of physiological processes under normal or stress conditions. Similarly, such in vivo amounts derivable from the oral administrations described previously include, for example, kinetics for nutrient uptake, clearance and half-life. Therefore, administration regimes can include dosing intervals shorter or longer than one or more times daily.

For example, depending on the weight of the recipient, effective amounts can be administered once or twice daily for orally administered nutrient compositions of the invention. However, the nutrients can alternatively be produced, for example, in time released formulations that allow for a reduced administration schedule. Similarly, intravenous, subcutaneous or other like administrations also can be utilized with the nutrient compositions of the invention and administration schedule reduced or increased depending on the concentration of the nutrient formulation and amount given per administration. These and other formulations and modes of administration are well known to those skilled in the art. Durations that are particularly efficacious in augmenting immune strength or detoxifying functions include, for example, routine administrations between about 2-15 weeks, preferable between about 3-12 weeks and more preferably between about 5-7 weeks. Using the oral formulations described previously, such routine administrations can occur about one to four times daily over a course of about 6, 7, 8, 9, 10, 11, or 12 or more weeks, for example.

As described previously, the antioxidant nutrient compositions of the invention employed alone or in combination with additional vitamin or mineral nutrients can be used to augment immune strength or detoxification functions of physiological processes within an individual. As such, the nutrient compositions of the invention are applicable for facilitating the health maintenance of normal individuals, promoting healing of individuals with physiological disorders or diseases as well as to enhance the therapeutic benefit of patients with a wide variety of disorders or diseases. The exemplary indicators described previously as measures of immune strength and detoxification function are similarly applicable as indicators of health maintenance, healing as well as improvement of disorders or diseases conditions. Therefore, augmentation of a therapeutic treatment through combined treatment with a nutrient composition of the invention also can be measured with the previously describe indicators.

Exemplary physiological disorders or diseases applicable for augmentation of a therapeutic treatment by combining the treatment with administration of a nutrient composition of the invention include immune-mediated diseases, cancer, heart disease, chronic fatigue syndrome, neurodegenerative diseases or an infectious disease. Specific examples of such disorders or diseases include multiple sclerosis, lupus, rheumatoid arthritis, scleroderma, coronary artery disease, atherosclerotic vessel disease, Madalung's disease, neoplastic conditions, solid tumor malignancies, non-solid malignancies, Alzheimer's disease, Parkinson's disease, infectious hepatitis, toxic hepatitis, drug-induced hepatitis, herpes, human immunodeficiency virus (HIV) infection or acquired immunodeficiency syndrome (AIDS). Numerous other physiological disorders or diseases also are applicable for treatment with the nutrient compositions of the invention. Further, the nutrient compositions of the invention also can be used to promote longevity in normal or diseased individuals alike. Specific examples illustrating the applicability of combined administration of the nutrient compositions of the invention with ongoing drug therapy are described further below. Given the teachings and guidance provided herein, those skilled in the art will know, or can readily determine, those physiological disorders or diseases that can be augmented when combined with administration of a nutrient composition of the invention.

For example, as a class, the antioxidants described herein individually enhance T and B lymphocyte proliferation, decrease the release of lactic acid into the bloodstream, and enhance mitochondrial energy production (Kalebic et al., *Proc. Natl. Acad. Sci. USA* 88:986-990 (1991)). These effects also can be beneficial for preventing cell apoptosis, which occurs secondary to the increased oxidative stress found during HIV infection irrespective of whether infected individuals are undergoing nRTI therapy (Butte et al., *Immunol. Today* 15:7-10 (1994); Sato et al., *J. Immunol.* 154:3194-3203 (1995)). Combining effective amounts of at least one vitamin antioxidant, one mineral antioxidant and at least three high potency antioxidants results in, for example, cooperation between interdependent systems as well as performance of individual nutrient targets that leads to optimal tuning of immune strength and detoxification functions.

In addition, nucleoside reverse transcriptase inhibitors are known to inhibit mitochondrial DNA-polymerase gamma (Parker et al., *J. NIH Res.* 6:57-61 (1994); Chen et al., J. Biol. Chem. 264:11934-11937 (1989)). The resultant depletion of mitochondrial DNA contributes to a dysregulation of the cytochrome energy system of the electron transport chain. This functional uncoupling of oxidative metabolism creates a backup of acetyl Co-enzyme A, as well as lactic acid, both intracellularly and extracellularly. Release of these compounds into the blood leads to an increase in gluconeogenesis in the liver thereby producing increased serum insulin levels and concomitant hyperlipidemia (Khouri et al., *Infec. Med.* 17:547-554 (2000)). These physiologic effects contribute to an increase in truncal fat accumulation in HIV-infected patients. This process is commonly described as HIV-associated lipodystrophy syndrome.

Other disorders or diseases attributable to drug-induced mitochondrial toxicity such as that caused by nRTI include, for example, fat redistribution, hepatitis, anemia, pancreatitis, and peripheral neuropathy. This pathogenic mechanism is also linked to the development of life threatening lactic acidosis. While previously rare, lactic acidosis can be more common at present due to, for example, the large number of drugs currently used in combination, prolonged drug therapy, improved survival or combinations of these reasons.

The development of lactic acidosis also reflects a process of progressive hepatotoxicity, because lactic acid is normally converted into glucose by the liver, thereby lessening the amount in circulation. As such, lactic acidosis is a sign of mitochondrial toxicity or dysfunction because the mitochondria are the site of oxidative phosphorylation, which converts lactate into pyruvate, and pyruvate into carbon dioxide, water and ATP, in the electron transport chain. By inhibiting this process, drugs such as nRTI cause more pyruvate to back up with subsequent conversion in the cytoplasm into lactate. Inhibition of oxidative phosphorylation also inhibits the liver from clearing excess lactic acid in the serum.

The link between drug-induced mitochondrial toxicities and treatment with the nutrient compositions of the invention can be exemplified with reference to nRTI-induced toxicity. Mitochondria divide independently of cell division and are highly susceptible to nRTI-induced toxicity due to their inhibition of mitochondrial DNA polymerase gamma. The nutrient compositions of the invention function to inhibit this toxicity, reduce deleterious free radical buildup, promote liver detoxification functions and enhance energy production, all of which promote reduced toxicity within the mitochondria.

Similarly, mitochondrial toxicity also is linked to peripheral neuropathy (PN). PN is a disease or degenerative state of the peripheral nerves in which motor, sensory, or vasomotor nerve fibers may be affected and which is marked by muscle weakness and atrophy, pain, and numbness. PN occurs in about 10% or more of patients beginning antiretroviral therapy with either stavudine (D4T) or didanosine (DDI) containing antiviral regimens (Simpson et el., *Ann. Intern. Med.* 121:769-785 (1994)). Stavudine and didanosine inhibit the production of mitochondrial DNA in peripheral neurons, which leads to a buildup of free oxygen species that can be toxic and lead to mitochondrial dysfunction. Buildup of free oxygen species can be one factor for drug-induced peripheral neuropathy such as that caused by nRTI medications (Chen et al., *Mol. Pharmacol.* 39:625-628 (1991)).

As described previously, healthy mitochondrial functioning is dependent, in part, on nutrients. Acetyl L-carnitine is utilized to ferry fatty acids across the mitochondrial membrane for fuel. N-acetyl-cysteine (NAC) and alpha-lipoic acid are utilized to neutralize the oxidation byproducts of energy metabolism such as those caused by free radicals. Vitamins C, E, and selenium are similarly utilized for the neutralization of free radicals. If some or all of these nutrient-dependent pathways becomes depleted, increased mitochondrial toxicity leading to programmed cell death is more likely to occur (Butte et al., *Immunol. Today* 15:7-10 (1994)).

Furthermore, dietary supplementation with alpha-lipoic acid or acetyl L-carnitine can possibly decrease the extent of peripheral neuropathy occurring in diabetes mellitus or HIV infection (Ziegler et al. *Exp. Clin. Endocrinol. Diabetes* 107: 421-30 (1999); Ziegler et al., Diabetes 46 Suppl 2:S62-66 (1997); Scarpini et al., *J. Peripher. Nerv. Syst.* 2:250-52 (1997); Famularo et al., *J. Peripher. Nerv. Syst.* 3:227-29 (1998)). Vitamin B6 has also been studied as an treatment intervention for carpal tunnel syndrome, which also is a form of neuropathy (Bernstein et al., *J. Am. Coll. Nutr.* 12:73-76 (1993)). Combining effective amounts of at least one vitamin antioxidant, one mineral antioxidant and at least three high potency antioxidants results in, for example, cooperation enhancement of immune strength or detoxification functions that leads to optimal performance of these systems for enhanced treatment or reduction in the severity of mitochondrial toxicities such as PN.

Other drug-induced mitochondrial toxicities include, for example, hepatitis, anemia, peripheral neuropathy, pancreatitis, cardiomyopathy, HIV protease inhibitor oxidative stress, oxidative stress secondary to other HIV therapeutics and fat redistribution, all of which are applicable for treatment with a nutrient composition of the invention. Nutrient treatment for these and other diseases can be administered alone or in combination with another therapeutic drug regimen.

Mitochondrial toxicity induced by other insults or conditions also can be treated with the nutrient compositions of the invention. Administering a nutrient composition alone or in combination with an applicable therapy will augment the immune strength or detoxification functions of the recipient individual including, for example, reducing mitochondrial oxidative stress, oxidative damage or increasing energy production. Exemplary insults or conditions other than drug induced processes that can result in mitochondrial toxicity include, for example, radiation poisoning, ischemic events, other acute events or chronic events. All of such insults or conditions can result in, for example, mitochondrial shock, oxidative stress or oxidative damage. Augmentation of immune strength, detoxification functions or both can reduce the severity of symptoms resulting from these occurrences by, for example, increasing energy levels, promoting a balanced physiological state or reducing free radical buildup.

Therefore, the invention provides a method of augmenting a therapeutic treatment of a disease. The method consists of administering to an individual a nutrient composition of the invention one or more times a day over a period of about 5-7 weeks, wherein immune system function is stimulated to result in an increase of CD4$^+$ cells of at least about 15% compared to pre-administration levels.

The invention also provides a method of augmenting a therapeutic treatment of a disease comprising administering to an individual a composition of the invention one or more times a day over a period of about 5-7 weeks, wherein a physiological detoxification function is stimulated to result in a decrease of one or more free radical markers by about 20% compared to pre-administration levels.

The nutrient compositions useful in the methods of the invention include an optimal combination of an effective amount of at least one vitamin antioxidant, at least one mineral antioxidant and a highly saturable amount of at least three high potency antioxidants. The at least one vitamin antioxidant can be vitamin C, bioflavonoid complex, vitamin E, vitamin B6 or beta-carotene and the at least one mineral antioxidant can be zinc or selenium. The at least three high potency antioxidants can be alpha lipoic acid, acetyl L-carnitine, N-acetyl-cysteine, co-enzyme Q10 or glutathione. Nutrient compositions useful in the methods of the invention also include an optimal combination of an effective amount of at least three vitamin antioxidants, at least two mineral antioxidants and a highly saturable amount of at least three high potency antioxidants. The at least three vitamin antioxidants can be three vitamins selected from vitamin C, bioflavonoid complex, vitamin E, vitamin B6 or beta-carotene. The at least two mineral antioxidant can be zinc and selenium and the at least three high potency antioxidants can be three antioxidants selected from alpha lipoic acid, acetyl L-carnitine, N-acetyl-cysteine, co-enzyme Q10 or glutathione. Purity levels of the nutrient compositions can be 99% or greater by total weight. Further provided is a nutrient composition useful in the methods of the invention that consists of an optimal combination of an effective amount of vitamin C, bioflavonoid complex, vitamin E, zinc, selenium, alpha lipoic acid, acetyl L-carnitine and N-acetyl-cysteine.

Augmentation of therapeutic treatment provided by the invention include treatments for immune-mediated disease, cancer, heart disease, chronic fatigue syndrome, neurodegenerative diseases or an infectious disease. Specific examples of such disorders or diseases include multiple sclerosis, lupus, rheumatoid arthritis, scleroderma, coronary artery disease, atherosclerotic vessel disease, Madalung's disease, neoplastic conditions, solid tumor malignancies, non-solid malignancies, Alzheimer's disease, Parkinson's disease, infectious hepatitis, toxic hepatitis, drug-induced hepatitis, herpes, human immunodeficiency virus (HIV) infection or acquired immunodeficiency syndrome (AIDS) as well as for the promotion of longevity in normal or diseased individuals.

It is understood that modifications which do not substantially affect the activity of the various embodiments of this invention are also included within the definition of the invention provided herein. Accordingly, the following examples are intended to illustrate but not limit the present invention.

Example I

Nutrient Supplementation Treatment in Patients with Peripheral Neuropathy Induced by Stavudine or Didanosine Antiviral Therapy This Example shows the effectiveness and non-toxicity of a broad-spectrum, nutrient treatment for medication-induced peripheral neuropathy in HIV-infected patients.

A clinical study was performed to assess the beneficial effects of an antioxidant, multinutrient formula designed to lessen the systemic clinical effects of mitochondrial toxicity, including symptoms of PN, in HIV-infected individuals undergoing a stable, D-drug-containing highly active antiretroviral therapy (HAART). The design of the study consisted of a randomized, double-blind, placebo-controlled, clinical trial to assess the use of nutrient supplementation compared to a placebo in the treatment of stavudine and/or didanosine-induced peripheral neuropathy in patients with HIV infection. A 1:1 randomized patient to placebo ratio was analyzed using a total of 40 patients that were enrolled in the study.

HIV-infected patients enrolled in the study were required to meet several inclusion criteria. In contrast, a number of exclusion criteria prevented HIV-infected individuals from enrolling in the clinical study. There were seven inclusion criteria for selecting individuals for enrollment. These inclusion criteria required enrollees to have: (1) an active HIV infection, where positive diagnosis of HIV was based on the medical history, clinical signs and symptoms, or results of laboratory testing; (2) a CD4$^+$ cell count greater or equal to 100 cells/mm$^3$; (3) the presence of lower extremity peripheral neuropathy, based on history and physical exam since starting to take stavudine and/or didanosine; (4) receiving current treatment with the antiviral therapeutics stavudine (D4T), didanosine (DDI) or both; (5) at least 18 years of age; (6) women of child bearing potential were required to have a negative pregnancy test within two weeks prior to randomization and agree to practice barrier method birth control during the study period, and (7) willingness and ability to sign an informed consent statement and to comply with the protocol.

There were 11 exclusion criteria that prevented HIV-infected individuals from enrollment in the clinical study. These exclusion criteria removed potential enrollees from consideration where the individual: (1) had a known allergy or intolerance to any nutrient supplements contained in the nutrient composition; (2) was pregnant; (3) was undergoing active treatment for an acute opportunistic infection or malignancy, except for non-systemic treatment of Kaposi's Sarcoma; (4) had a CD4$^+$ cell count of less than 100 cells/mm$^3$; (5) exhibited vitamin B12 deficiency; (6) exhibited an alanine aminotransferase (ALT) greater than 10× the normal range; (7) had serum creatinine greater than or equal to 2.0 mg/dL; (8) was receiving recombinant human growth hormone therapy during the previous week, during the period of the clinical study or those on prior therapy unable to "wash out" during the period between the screening and baseline visits; (9) was receiving any pharmacologic treatment for peripheral neuropathy during the previous week or unable to "wash out" prior to baseline measurements, including both prescription and non-prescription-strength non-steroidal anti-inflammatory drugs (NSAIDS), narcotic and non-narcotic analgesics, tricyclic antidepressants, and anticonvulsant medications such as gabapentin (Neurontin); (10) was receiving acupuncture and/or massage therapy, specifically to treat peripheral neuropathy symptoms, during the previous four weeks, and (11) was receiving current nutrient or herbal supplements greater than one multivitamin pill per day.

Patients enrolled in the study received one nutrient packet twice daily at the beginning of a meal. Each nutrient packet included: (1) a multivitamin composition; (2) a multimineral composition; (3) vitamin B6 at 130 mg; (4) acetyl L-carnitine at 500 mg; (5) alpha-lipoic acid at 200 mg; (6) N-acetyl cysteine at 600 mg. Each placebo nutrient packet included an identical appearing packet of placebo capsules.

Several quantitative and qualitative criteria were evaluated to assess the efficacy of the nutrient compositions following administration. Briefly, changes in pain intensity at 4, 8, and 12 weeks of treatment were assessed by the Neuropathy Inventory Linear Analog Scale (NILAS). Changes in quality of life at 4, 8, and 12 weeks of treatment were assessed by both the Linear Analog Scale Assessment (LASA) and the Medical Outcomes HIV Health Survey (MOS-HIV). Similarly, changes in the neurological examination at 4, 8, and 12 weeks of treatment were assessed by the Neurologic Examination Assessment Tool (NEAT). The percentage of patients in each group able to continue their original antiviral medications at 4, 8, and 12 weeks of treatment was another criteria evaluated as was the percentage of patients in each group able to avoid taking prescription strength pain medications at each of these time periods. Finally, changes in metabolic and immunologic measurements including, for example, CD4$^+$ cell count, HIV RNA, fasting plasma lactate, fasting lipid panel, fasting insulin level, fasting glucose level, and liver function tests in each group also were measured at 4, 8, and 12 week intervals following initiation of treatment.

Forty (40) patients were actually enrolled in the study. All patients exhibited symptomatic peripheral neuropathy and were undergoing either stavudine or didanosine therapy. This group was randomly assigned to ingest either a nutrient composition as described below or a placebo packet twice daily. The duration of nutrient treatment lasted 12 weeks in double blinded fashion at four research centers in the US. The baseline or nutrient pretreatment characteristics of the patients taking either the nutrient composition or a placebo are shown below in Table 1. A description of the test parameters and methods are described further below in conjunction with the results of the study.

TABLE 1

Baseline Demographics and Clinical Characteristics

| Variable | Placebo (n = 22) | Nutrients Composition (n = 18) |
|---|---|---|
| Mean age | 46.6 | 45.6 |
| Mean CD4 count (cells) | 467 | 357 |
| Viral load (log10) | 2.4 | 2.3 |
| On Stavudine (D4T) (%) | 54% | 66% |
| On Didanosine (DDI) (%) | 23% | 17% |
| On Both (D4T and DDI) (%) | 23% | 17% |
| Neuropathy Score (0 to 100) {NILAS} (100 = severe neuropathy symptoms) | 57 | 52 |
| QOL Score (0 to 100) {LASA} (100 = ideal energy & QOL) | 42 | 48 |

Implementation of the study required patients to continue therapy with a stable HAART regimen and also not to consume any nutrients other than those administered in excess of one low-dose multivitamin pill per day. The nutrient composition tested included substantial daily dosages of 3 potent antioxidants. These potent antioxidants were acetyl L-carnitine at 1,000 mg/day, N-acetyl cysteine at 1,200 mg/day and alpha lipoic acid at 400 mg/day. The composition also contained a variety of other vitamins and minerals all in excess of the suggested RDA requirements. The complete formulation and total daily dose of the nutrient composition is shown below in Table 2.

The nutrient compositions were manufactured according to the dry weights specified in FIG. 1. Manufacturing fillers, binders or lubricants, such as stearates, palmitates or other substances which can be inhibitory to absorption, bioavailability or tolerance of compounds in individuals, were omitted from the nutrient compositions. Purity levels of the nutrient compositions were about 99 percent of total weight of the formulation.

Patients were assessed over a 12 week treatment for the quantitative and qualitative indicators described previously. Measurements or observations occurred at four-week intervals throughout the course of the study. Statistical analyses were executed using two sided t-tests with an alpha level of 0.05. No adjustments were made for multiple comparisons and missing values were imputed using a last-observation-carried-forward method.

TABLE 2

Nutrient Composition (Total Daily Dosages)

| Multivitamin/Multimineral | | | |
|---|---|---|---|
| Beta Carotene | 20,000 i.u. | Calcium | 800 mg |
| Vitamin C | 600 mg | Iron | 18 mg |
| Vitamin D | 400 i.u. | Iodine | 150 mcg |
| Vitamin E | 800 i.u. | Magnesium | 400 mg |
| Vitamin B1 | 60 mg | Zinc | 30 mg |
| Vitamin B2 | 60 mg | Selenium | 200 mcg |
| Vitamin B6 | 260 mg | Copper | 2.0 mg |
| Niacinamide | 60 mg | Manganese | 10 mg |
| Folic acid | 800 mcg | Chromium | 100 mcg |
| Vitamin B12 | 2.5 mg | Molybdenum | 300 mcg |
| Biotin | 50 mcg | Choline | 60 mg |
| Inositol | 60 mg | Glutamic acid | 100 mg |
| Pantothenic acid | 60 mg | Boron | 2.0 mg |
| Potassium | 99 mg | Betaine HCL | 150 mg |
| Vitamin A | 8,000 i.u. | Bioflavinoid complex | 300 mg |
| Additional Antioxidants | | | |
| Alpha lipoic Acid | 400 mg | | |
| N-acetyl cysteine (NAC) | 1200 mg | | |
| Acetyl L-carnitine | 1000 mg | | |

Results obtained for the primary and secondary endpoint measurements are described below. Briefly, the effect of nutrient treatment on Neuropathy Inventory Linear Analog Scale (NILAS) was assessed. The NILAS tool assesses pain intensity on a visual analog scale. The responses to each of three questions were transformed to a 0-100 scale such that a higher score indicates more pain. Each question was reported individually and the mean of the three questions was calculated to form an overall score. The results from this study indicate that the invention diminished the overall symptoms of peripheral neuropathy (pain, numbness, paresthesias) by 41.5% from baseline (on-treatment analysis).

Also assessed was the effect of nutrient treatment on quality of life using Linear Analog Scale Assessment (LASA). The LASA tool assesses quality of life as measured on a visual analog scale. The responses to each of three questions were transformed to a 0-100 scale such that a higher score indicates a higher quality of life. Each question was reported individually and the mean of the three questions was calculated to form an overall score. The results from this study indicate that the invention improved the overall quality of life (energy level, daily activities, overall quality of life) by 29% from baseline (on-treatment analysis). The results indicate that HIV-infected individuals with long standing PN showed substantial improvements in both linear pain scale and quality of life measurements (41.5% and 29%, respectively) during twelve weeks of taking this micronutrient formula. A statistically significant difference from placebo was not revealed, possibly due to a small sample size.

The effect nutrient treatment on HIV viral load as determined by HIV RNA measurements was also assessed. Viral RNA was measured by a commercial diagnostic service (Immunodiagnostic Laboratories (San Leandro, Calif.)). Table 3 shows the mean change in HIV RNA at the measured time points compared to pretreatment measurements. The patients receiving treatment with the nutrient composition showed a trend toward decreasing HIV RNA over twelve weeks of taking this nutrient formula. Specifically, patients taking the nutrient composition experienced a decline of about 4,755 copies in HIV RNA viral load compared to an increase of about 7,412 copies in HIV RNA viral load in patients taking the placebo. A statistically significant difference from placebo was not revealed, possibly due to a small sample size.

TABLE 3

Effect of Nutrient Composition on HIV RNA Viral Load

| On Treatment | Day 1 | Week 4 | Week 8 | Week 12 |
|---|---|---|---|---|
| Mean Change in HIV RNA (placebo) | 0 | 8494 | 7389 | 7412 |

TABLE 3-continued

Effect of Nutrient Composition on HIV RNA Viral Load

| On Treatment | Day 1 | Week 4 | Week 8 | Week 12 |
|---|---|---|---|---|
| Mean Change in HIV RNA (nutrients) | 0 | −5135 | −477 | −4755 |

The effect of nutrient treatment on CD4+ cell count was also assessed. One CD4+ cell measurement determined the change in total number of CD4+ cells at the indicated treatment points compared to CD4+ cell numbers prior to treatment. Briefly, the total CD4+ cell count was determined by immunoaffinity binding performed by a commercial service (Immunodiagnostic Laboratories (San Leandro, Calif.)). Table 4 shows the results of these measurements and indicate that the patients taking the nutrient composition sustained a 64 cell rise in absolute CD4+ cell counts when compared to a 13 cell rise in patients taking the placebo.

TABLE 4

Effect of Nutrient Composition on Absolute CD4+ Cell Counts

| On Treatment | Day 1 | Week 4 | Week 8 | Week 12 |
|---|---|---|---|---|
| Mean Change in CD4 Count (placebo) | 0 | −15 | −5 | 13 |
| Mean Change in CD4 Count (nutrients) | 0 | 44 | 68 | 64 |

Another CD4+ cell assessment calculated the percent change in CD4+ cells compared to pretreatment values. CD4+ cells were determined as described above for FIG. 7. Results showing a mean change percentage of CD4+ cell compared to baseline levels are shown in Table below. The nutrient treated group showed a steady and statistically significant rise in CD4 counts over twelve weeks. Patients taking this nutrient composition had an average increase of 26% in their CD4+ cell counts compared to 2% in those taking a placebo (p<0.03 OT).

TABLE 5

Mean Change from Baseline in CD4 (%)
CD4 increase from baseline (%)

| Time Point | Placebo | Nutrient Composition |
|---|---|---|
| Baseline | — | — |
| Week 4 | <1 | 14 |
| Week 8 | <1 | 20 |
| Week 12 | 2 | 26 (p < 0.05) |

The effects of nutrient treatment on fasting lipids, glucose, serum lactate and ALT levels were also assessed. Each of these tests represent direct and indirect measurements of metabolic toxicities which can be seen as a result of either HIV disease, antiretroviral therapy, or both. In this study, they were measured to identify a potentially positive or negative effect of the invention on each parameter. The study results indicated that all of these parameters (fasting lipids, insulin, glucose, serum lactate and ALT) were not adversely affected in patients taking the nutrient composition.

The overall tolerability of the nutrient compositions described above was also determined. The results indicate that daily administration of the nutrient composition over a 12 week course of treatment is safe for HIV-infected patients who are taking D4T, DDI or both antiretroviral therapeutics.

There were two adverse events reported which occurred in the treatment group. These events were bacterial pneumonia and a cystic lithiasis. However, both were judged unrelated to the nutrient treatment and both patients recovered uneventfully. Of note was that there were no reported gastrointestinal (GI) side effects from the group taking either the placebo or nutrient compositions.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method of increasing a mammal's CD4+ cell count while undergoing therapy for treatment of a condition selected from the group consisting of immune-mediated diseases, cancer, heart disease, neurodegenerative disease, and infectious disease, comprising:
    administering to the mammal, during a treatment period, a nutrient composition and at least one drug effective for treatment of said condition;
    the nutrient composition comprising, in per kg body weight per day:
        1.43 mg to 11.42 mg alpha lipoic acid;
        3.57 mg to 28.58 mg acetyl L-carnitine; and
        4.28 mg to 34.28 mg N-acetyl-cysteine;
    whereby the mammal's CD4+ cell count is increased during the treatment period.

2. The method of claim 1, wherein the nutrient composition further comprises one or more vitamins or minerals selected from the group consisting of zinc, selenium, vitamin C, bioflavinoid complex, vitamin E, beta-carotene, vitamin A, vitamin B1, vitamin B2, vitamin B6, niacinamide, calcium panthothenate, folic acid, vitamin B12, copper, manganese, chromium, and molybdenum.

3. The method of claim 1, wherein the alpha-lipoic acid, acetyl L-carnitine, and N-acetyl-cysteine are present in the nutrient composition in a ratio from 1:1:1 to 1:4:6.

4. The method of claim 1, wherein the treatment period is from about three to about twelve weeks.

5. The method of claim 1, wherein the treatment period is at least fifteen weeks.

6. The method of claim 1, wherein the nutrient composition is administered orally from one to four times per day.

7. The method of claim 1, wherein the nutrient composition further comprises one or more antioxidants selected from the group consisting of co-enzyme Q10 and glutathione.

8. The method of claim 2, wherein the nutrient composition further comprises one or more vitamins or minerals selected from the group consisting of choline, inositol, biotin, vitamin D3, calcium, magnesium, iron, iodine, potassium, boron, betaine, and glutamic acid.

9. The method of claim 1, wherein the mammal's CD4+ cell count increases by at least 25% compared to pre-administration levels.

10. The method of claim 1, wherein the mammal's CD4+ cell count increases by at least 40% compared to pre-administration levels.

11. The method of claim 1, wherein said condition is selected from the group consisting of multiple sclerosis, lupus, rheumatoid arthritis, scleroderma, coronary artery disease, atherosclerotic vessel disease, Madalung's disease, neoplastic conditions, solid tumor malignancies, non-solid malignancies, Alzheimer's disease, Parkinson's disease, infectious hepatitis, toxic hepatitis, drug-induced hepatitis, herpes, human immunodeficiency virus (HIV) infection, and acquired immunodeficiency syndrome (AIDS).

12. A method of treating a human patient suffering from HIV infection or cancer while increasing the patient's CD4+ cell count, comprising:
   administering to the patient at least one anti-retroviral drug; and
   administering to the patient a nutrient composition comprising, in per patient kg body weight per day:
   1.43 mg to 11.42 mg alpha lipoic acid;
   3.57 mg to 28.58 mg acetyl L-carnitine; and
   4.28 mg to 34.28 mg N-acetyl-cysteine.

13. The method of claim 12, wherein the nutrient composition further comprises one or more vitamins or minerals selected from the group consisting of zinc, selenium, vitamin C, bioflavinoid complex, vitamin E, vitamin A, and vitamin B.

14. The method of claim 12, wherein the nutrient composition further comprises at least one of glutathione and co-enzyme Q10.

15. The method of claim 13, wherein the nutrient composition further comprises one or more vitamins or minerals selected from the group consisting of beta-carotene, vitamin B1, vitamin B2, niacinamide, calcium panthothenate, choline, inositol, folic acid, biotin, vitamin D3, vitamin B12, calcium, magnesium, iron, iodine, copper, manganese, potassium, chromium, molybdenum, boron, betaine, and glutamic acid.

16. The method of claim 12, wherein the nutrient composition further comprises a vitamin antioxidant selected from the group consisting of vitamin B6 and beta-carotene.

17. The method of claim 12, wherein the patient's CD4+ cell count is increased by at least 25% compared to pre-administration levels.

18. The method of claim 12, wherein the patient's CD4+ cell count is increased by at least 40% compared to pre-administration levels.

19. The method of claim 12, wherein the at least one anti-retroviral drug is a reverse transcriptase inhibitor.

20. The method of claim 19, wherein the reverse transcriptase inhibitor is a nucleoside inhibitor.

21. The method of claim 12, wherein the at least one anti-retroviral drug is an HIV protease inhibitor.

22. The method of claim 12, wherein the anti-retroviral drug is selected from the group consisting of stavudine or didanosine.

23. A nutrient composition comprising a daily dosage of at least:
   400 mg alpha lipoic acid;
   1000 mg acetyl L-carnitine;
   1200 mg N-acetyl-cysteine; and
   wherein the alpha-lipoic acid, acetyl L-carnitine, and N-acetyl-cysteine are present in the nutrient composition in a ratio from 1:1:1 to 1:4:6.

24. The composition of claim 23, further comprising one or more vitamins or minerals selected from the group consisting of zinc, selenium, vitamin C, bioflavinoid complex, vitamin E, beta-carotene, vitamin A, vitamin B1, vitamin B2, vitamin B6, niacinamide, calcium panthothenate, folic acid, vitamin B12, copper, manganese, chromium, and molybdenum.

25. The composition of claim 23, wherein the daily dosage is in tablet form comprising a total of up to 6 tablets per day.

26. The composition of claim 25, wherein the tablets comprise at least one multivitamin tablet and at least one multi-mineral tablet.

27. The composition of claim 23, further comprising one or more antioxidants selected from the group consisting of co-enzyme Q10 and glutathione.

28. The composition of claim 23, further comprising one or more vitamins or minerals selected from the group consisting of choline, inositol, biotin, vitamin D3, calcium, magnesium, iron, iodine, potassium, boron, betaine, and glutamic acid.

29. The composition of claim 23, further comprising vitamin B6 and beta-carotene.

\* \* \* \* \*